(12) United States Patent
Kolossváry

(10) Patent No.: US 6,178,384 B1
(45) Date of Patent: Jan. 23, 2001

(54) METHOD AND APPARATUS FOR SELECTING A MOLECULE BASED ON CONFORMATIONAL FREE ENERGY

(75) Inventor: István Kolossváry, Madison, NJ (US)

(73) Assignee: The Trustees of Columbia University in the City of New York, New York, NY (US)

(*) Notice: Under 35 U.S.C. 154(b), the term of this patent shall be extended for 0 days.

(21) Appl. No.: 08/940,145

(22) Filed: Sep. 29, 1997

(51) Int. Cl.[7] .................................................... G06F 19/00
(52) U.S. Cl. ............................. 702/27; 702/32; 703/11; 703/12
(58) Field of Search ........................... 702/27, 30, 19, 702/22, 32, FOR 115–FOR 119; 434/278, 279, 298; 540/456, 460; 560/25, 18; 364/578; 436/86, 89; 502/167; 706/924; 700/266, 268, 269; 703/11, 12

(56) References Cited

U.S. PATENT DOCUMENTS

| | | | |
|---|---|---|---|
| 5,265,030 | * 11/1993 | Skolnick et al. | 702/27 |
| 5,740,072 | * 4/1998 | Still et al. | 702/27 |
| 5,784,294 | * 7/1998 | Platt et al. | 702/27 |

OTHER PUBLICATIONS

Burger et al., (1994) J. Am. Chem. Soc. 116: 3593–3594, (No Month). Free Energy Calculations in Molecular Design: Predictions by Theory and Reality by Experiment with Enantioselective Podand Ionophores.

Gilson et al., Biophys. J. 72: 1048–1069. (Mar. 1997).The Statistical–Thermodynamic Basis for Computation of Binding Affinities: A Critical Review.

Gilson et al., (Chemistry & Biology 4: 87–92. (Feb. 1997). A New Class of Models for Computing Receptor–Ligand Binding Affinities.

Go et al., Proc. Natl. Acad. Sci. USA 80:3696. (Feb. 1983). Dynamics of a Small Globular Protein in Terms of Low–Frequency Vibrational Modes.

(List continued on next page.)

*Primary Examiner*—Hal Wachsman
(74) *Attorney, Agent, or Firm*—John P. White; Cooper & Dunham LLP

(57) ABSTRACT

A method of using a computer processor to analyze electrical signals and data representative of a first molecule to determine conformational free energy of the first molecule so as to determine whether the first molecule is more stable than a second molecule, wherein both molecules have a predefined connectivity and exist in a predefined environment, includes generating a set of data representative of low-energy minimum conformations of the first molecule derived from connectivity of the first molecule, a potential energy function, and a conformational search method. Conformational free energy of the first molecule is determined by calculating a configuration integral in all degrees of freedom based upon a contribution of each conformation of the set of conformations of the first molecule, and the configuration integral is calculated by performing importance sampling multidimensional Monte Carlo integration over a multidimensional volume enclosing a current conformation of the first molecule in a conformational space, repeating the integration for each conformation in the set of data, and summing the conformational contributions so as to determine a total configuration integral for the first molecule and thereby determine the conformational free energy of the first molecule.

38 Claims, 8 Drawing Sheets

OTHER PUBLICATIONS

Head et al. J. Phys. Chem. A. 101:1609–1618. (Feb. 1997). "Mining Minima": Direct Computation of Conformational Free Energy.

Karplus et al., (1981)Macromolecules 14:325–332. Method for Estimating the Configurational Entropy of Macromolecules. (No Month).

Kolossváry, et al. J. Am. Chem. Soc. 118:5011–5019 Mar. 1996. Low Mode Search. An Efficient, A Automated Computational Method for Conformational Analysis.

Kolossváry et al. (1993) J. Am. Chem. Soc. 115:2107–2119; Comprehensive Conformational Analysis of the Four– to Twelve–Membered Ring Cycloalkanes (No Month).

Lepage et al., (1978) J. Comput. Phys. 27:192–203; A New Algorithm for Adaptive Multidimensional Integration. (No Month).

Levy et al., (1984) Macromolecules 17: 1370–1374, Evaluation of the Configurational Entropy for Proteins: Application to Molecular Dynamics Simulations of a α–Helix. (No Month).

Liu et al. (1993) Tetrahedron Letters 34: 2573–2576, Highly Selective Binding of Diverse Neutral Donor/Acceptor Substrates by a $C_3$ Macrotricyclic Receptor. (No Month).

McDonald et al. (1996) J. Am. Chem. Soc. 118: 2073–2077; Application of Free Energy Perturbation Calculations to the Enantioselective Binding of Peptides to $C_3$Symmetric Synthetic Receptors. (No Month).

Press et al., (1992) Numerical Recipes in C Second Edition. New York: Cambridge University Press, pp. 313–318. (No Month).

Roitberg et al., (1997) J. Phys. Chem. B. 101: 1700–1706, A Vibrational Eigenfunction of a Protein: Anharmonic Coupled–Mode Ground and Fundamental Excited States of BPTI. (Feb. 1997).

Roitberg et al., (1995) Science 268: 1319–1322 Anharmonic Wave Function of Proteins: Quantum Self–Consistent Field Calculations of BPTI. (Jun. 1995).

Senderowitz et al. (1996) J. Am. Chem. Soc. 118: 2078–2086, Carbohydrates: United Atom AMBER* Parameterization of Pyranoses and Simulations Yielding Anomeric Free Energies. (No Month).

Senderowitz et al. (1995) J. Am. Chem. Soc. 117: 8211–8219, A Smart Monte Carlo Technique for Free Energy Simulation of Muliconformational Molecules. (No Month).

Still et al. (1993) Phil. Trans. R. Soc. Lond. A. 345: 97–104, Synthetic Receptors for Peptides. (No Month).

Still et al., (1990) J. Am. Chem. Soc. 112:6127–6129, Semianalytical Treatment of Solvation for Molecular Mechanics and Dynamics. (No Month).

Straatsma et al., (1992) Ann. Rev. Phys. Chem. 43: 407, Computational Alchemy. (No Month).

* cited by examiner 3-(L-7)

3-(D-7)

METHOD AND APPARATUS FOR SELECTING A MOLECULE BASED ON CONFORMATIONAL FREE ENERGY

BACKGROUND OF THE INVENTION

One of the key issues in chemistry is chemical stability. If chemical stability could be reliably predicted by computational methods, then real molecular engineering could be achieved being able to design stable molecules or molecular complexes having desirable properties rationally. One of the most important industries recently endeavored in molecular engineering is the pharmaceutical industry. Thanks to recent advances in molecular biology, the three-dimensional molecular structures of many biological target proteins are now known and it has been assumed that knowledge of the structure of the target protein could be used to rationally select the most active hypothetical molecules for actual synthesis for testing their applicability as potential drugs. The key factor of the activity of a drug molecule is the stability of its complex with a particular protein. The stability of the complex is measured by the binding free energy. The prediction of the relative binding energies of different drug candidates with respect to the same protein host is one of the most sought after hopes of the pharmaceutical industry. There, chemists often hypothesize dozens of molecules they might synthesize but have trouble deciding which ones have the best chance of being highly active in some biological assay. Computational techniques that help the chemists selecting the most promising candidates for synthesis are extremely valuable. Unfortunately, the thermodynamics of binding is quite complex (see, e.g. Gilson, M. K.; Given, J. A.; Bush, B. L.) and using the state-of-the-art arsenal of computational methods requires very long computer simulations (Kollman, P. A. 1993).

For calculations of the relative binding energies of different drugs for a given protein receptor to work properly, many different things have to be done correctly. In particular, the gas phase potential energy force field has to be accurate, the effect of solvent has to be included in some realistic and efficient way, and all the vibrational and conformational states of the system have to be sampled with the correct Boltzmann weights. This last issue is known as the sampling problem and is a particularly difficult one to solve because the drug-receptors complex may exist in many different conformations. Furthermore, these different conformations may be separated by large energy barriers that prevent these conformations from being interconverted using traditional simulation methods. Recent studies (e.g. van Gunsteren and Mark,1992) suggest that the length of contemporary free energy simulations of flexible biological molecules may be orders of magnitude too short for convergence and any agreement with experiment may be only fortuitous (i.e. not predictive). The invention described here should provide a solution to this problem by affording a direct method for the calculation of conformational and binding free energies without the need for expensive simulations.

Chemical stability can always be formulated in terms of conformational free energy (CFE) differences. There can be various levels envisioned at which approximations to CFE differences can be made. For example, if one wishes to calculate the anomeric free energy for the equilibrium of $\alpha$ and $\beta$ anomers of monosaccharides, then the simplest approach one can follow is to calculate the energy difference between the lowest energy $\alpha$ and the lowest energy $\beta$ anomer. Of course, this approach ignores entropic effects due to the fact that there are multiple conformations of both the $\alpha$ and $\beta$ anomers and that the individual conformations are not static (confined to the bottom of their energy well) but exhibit large dynamic diversity in terms of conformational changes limited to that energy well. Note that glucose, for example, possesses literally hundreds of low-energy conformations of both anomeric states.

Throughout this application, the following references are referred to by name and date within parentheses in the text; disclosures of these publications in their entireties are hereby incorporated by reference into this application to more fully describe the state of the art to which this invention pertains.

References

Allinger, N. L. *J. Am. Chem. Soc.* 1977, 99, 8127–8134.
Allinger, N. L.; Yuh, Y. H.; Lii, J.-H. *J. Am. Chem. Soc.* 1989, 111, 8551–8566.
Asensio, J. L.; Jimenez-Barbero, J. *Biopolymers* 1995, 35, 55.
Burger, M. T.; Armstrong, A.; Guarnieri, F.; McDonald, D. Q.; Still, W. C. *J. Am. Chem. Soc.* 1994, 116, 3593–3594.
Cornell, W. D.; Cieplak, P.; Bayly, C. I.; Gould, I. R.; Merz, K. M.; Ferguson, D. M.; Spellmeyer, D. C.; Fox, T.; Caldwell, G. W.; Kollman, P. A. *J. Am. Chem. Soc.* 1995, 117, 5179–5197.
Cramer, C. J.; Truhlar, D. G. *J. Am. Chem. Soc.* 1991, 113, 8305.
Csonka, G. I.; Éliás, K.; Csizmadia; I. G. *J. Comput. Chem.* 1997, 18, 330–342.
Edinger, S. R.; Cortis, C.; Shenkin, P. S.; Friesner, R. A. *J. Phys. Chem. B* 1997, 101, 1190–1197.
Eisenberg, D.; McLachlan, A. D. *Nature* 1986, 319, 199.
Eliel, L. E.; Wilen, S. H. *Stereochemistry of Organic Compounds;* Wiley-Interscience: New York, 1994; pp 696–702.
Gilson, M. K.; Given, J. A.; Head, M. S. *Chemistry & Biology* 1997, 4, 87–92.
Gilson, M. K.; Given, J. A.; Bush, B. L.; McCammon, J. A. *Biophys. J.* 1997, 72, 1047–1069.
Gilson, M.; Honig, B. *Proteins* 1988, 4, 7.
Glennon, T. M.; Zheng, Y. J.; Le Grand, S. M.; Shutzberg, B. A.; Merz, K. M. *J. Comput. Chem.* 1994, 15, 1019.
Go, N.; Noguti, T.; Nishikawa, T. *Proc. Natl. Acad. Sci. U.S.A.* 1983, 80, 3696.
Grootenhuis, P. D. J.; Haasnoot, C. A. G. *Mol. Simul.* 1993, 10, 75.
Ha, S. N.; Giammona, A.; Field, M.; Brady, J. W. *Carbohyd. Res.* 1988, 180, 207.
Ha, S.; Gao, J.; Tidor, B.; Brady, J. W.; Karplus, M. *J. Am. Chem. Soc.* 1991, 113, 1553.
Halgren, T. A. *J. Comput. Chem.* 1996, 17, 490–519.
Head, M. S.; Given, J. A.; Gilson, M. K. *J. Phys. Chem. A* 1997, 101, 1609–1618.
Hodge, C. N.; Zacharias, M.; McCammon, J. A. *J. Comput. Chem.* 1995, 16, 454–464.
Homans, S. W. *Biochemistry* 1990, 29, 9110.
Jeffrey, G. A.; Taylor, R. *J. Comput. Chem.* 1980, 1, 99.
Jorgensen, W. L.; Tirado-Rives, J. *J. Am. Chem. Soc.* 1988, 110, 1657–1666.
Jorgensen, W. L.; Chandrasekhar, J.; Madura, J. D.; Impey, R. W.; Klein, M. L. *J. Phys. Chem.* 1983, 79, 926.
Jorgensen, W. L.; Ravimohan, C. *J. J. Chem. Phys.* 1985, 83, 3050.
Kang, Y. K.; Némethy, G.; Scheraga, H. A. *J. Phys. Chem.* 1987, 91, 4105, 4109, 4118.
Karplus, M.; Kushick, J. N. *Macromolecules* 1981, 14, 325–332. (b) Levy, R. M.; Karplus, M.; Kushick, J.; Perahia, D. *Macromolecules* 1984, 17, 1370–1374.

Kollman, P. A. *Chem. Rev.* 1993, 93, 2395–2417.
Kolossváry, I.; Guida, W. C. *J. Am. Chem. Soc.* 1996, 118, 5011–5019.
Kolossváry, I.; Guida, W. C. *J. Am. Chem. Soc.* 1993, 115, 2107–2119.
Lepage, G. P. *J. Comput. Phys.* 1978, 27, 192–203.
Lipkowitz, K. B.; Raghothama, S.; Yang, J.-a. *J. Am. Chem. Soc.* 1992, 114, 1554.
Liu, R.; Still, W. C. *Tetrahedron Letters* 1993, 34, 2573–2576.
Mardsen, A.; Robson, B.; Thompson, J. S. *J. Chem. Soc., Faraday Trans.* 1 1988, 84, 2519.
Marten, B.; Kim. K.; Cortis, C.; Friesner, R. A.; Murphy, R. B.; Ringnalda, M. N.; Sitkoff, D.; Honig, B. *J. Phys. Chem.* 1996, 100, 11775–11788.
McDonald, D. Q.; Still, W. C. *Tetrahedron Lett.* 1992, 33, 7747.
McDonald, D. Q.; Still, W. C. *J. Am. Chem. Soc.* 1996, 118, 2073–2077.
Melberg, S.; Rasmussen, K. *Carbohyd. Res.* 1980, 78, 215.
Melberg, S.; Rasmussen, K. *J. Mol. Struct.* 1979, 57, 215.
Melberg, S.; Rasmussen, K. *Carbohyd. Res.* 1979, 76, 23.
Mohamadi, F.; Richards, N. G. J.; Guida, W. C.; Liskamp, R.; Lipton, M.; Caufield, C.; Chang, G.; Hendrickson, T.; Still, W. C. *J. Comput. Chem.* 1990, 11, 440.
Ooi, T.; Oobatake, M.; Némethy, G.; Scheraga, H. A. *Proc. Natl. Acad. Sci. U.S.A.* 1987, 84, 3086.
Press, W. H.; Teukolsky, S. A.; Vetterling, W. T.; Flannery, B. P. *Numerical Recipes in C Second Edition;* Cambridge University Press: New York, 1992; pp 316–328.
Qiu, D.; Shenkin, P. S.; Hollinger, F. P.; Still, W. C. *J. Phys. Chem. A* 1997, 101, 3005–3014.
Rasmussen, K. *Acta Chem. Scand.* 1982, A36, 323.
Reiling, S.; Schlenkrich, M.; Brickmann, J. *J. Comput. Chem.* 1996, 17, 450.
Roitberg, A.; Gerber, R. B.; Elber, R.; Ratner, M. A. *Science* 1995, 268, 1319–1322. (b) Roitberg, A. E.; Gerber, R. B.; Ratner, M. A. *J. Phys. Chem. B* 1997, 101, 1700–1706.
Rossky, P. J.; Karplus, M. *J. Am. Chem. Soc.* 1979, 101, 1913.
Schmidt, R. K.; Karplus, M.; Brady, J. W. *J. Am. Chem. Soc.* 1996, 118, 541.
Senderowitz, H.; Still, W. C. *J. Phys. Chem. B* 1997, 101, 1409–1412.
Senderowitz, H.; Parish, C.; Still, W. C. *J. Am. Chem. Soc.* 1996, 118, 2078–2086.
Senderowitz, H.; Guarnieri, F.; Still, W. C. *J. Am. Chem. Soc.* 1995, 117, 8211–8219.
Stewart, J. J. P. *QCPE J.* 1990, 11, 455.
Still, W. C.; Liu, R. *Phil. Trans. R. Soc. Lond. A* 1993, 345, 97–104.
Still, W. C.; Tempczyk, A.; Hawley, R. C.; Hendrickson, T. *J. Am. Chem. Soc.* 1990, 112, 6127–6129.
Straatsma, T. P.; McCammon, J. A. *Ann. Rev. Phys. Chem.* 1992, 43, 407.
Stroud, A. H. *Approximate Calculation of Multiple Integrals;* Prentice-Hall: Englewood Cliffs, N.J., 1971; Chapter 6.
van Eijck, B. P.; Hooft, R. W. W.; Kroon, J. *J. Phys. Chem.* 1993, 97, 12093.
van Gunsteren and Mark, Eur. J. Biochem. 1992, 204: 947–961
Warshel, A.; Russel, S. T. *Rev. Biophys.* 1984, 17, 283.
Weiner, S. J.; Kollman, P. A.; Case, D. A.; Singh, U. C.; Ghio, C.; Alagona, G.; Profeta Jr., S.; Weiner, P. *J. Am. Chem. Soc.* 1984, 106, 765–784.
Woods, R. J.; Dwek, R. A.; Edge, C. J.; Fraser-Reid, B. *J. Phys. Chem.* 1995, 99, 3832.
Zheng, Y.-J.; Le Grand, S. M.; Merz, K. M.; *J. Comput. Chem.* 1992, 13, 772.

SUMMARY OF THE INVENTION

The invention is directed to a method of using a computer processor to analyze electrical signals and data representative of a first molecule to determine conformational free energy of the first molecule so as to determine whether the first molecule is more stable than a second molecule, wherein both molecules have a predefined connectivity and exist in a predefined environment, comprising: (a) generating a set of data representative of low-energy minimum conformations of the first molecule derived from connectivity of the first molecule, a potential energy function, and a conformational search method; (b) determining conformational free energy of the first molecule by calculating a configuration integral in all degrees of freedom based upon a contribution of each conformation of the set of conformations of the first molecule, wherein the configuration integral is calculated by: (i) performing importance sampling multidimensional Monte Carlo integration over a multidimensional volume enclosing a current conformation of the first molecule in a conformational space, (ii) repeating step (i) for each conformation in the set of data; and (iii) summing the conformational contributions determined in steps (i–ii) so as to determine a total configuration integral for the first molecule and thereby determine the conformational free energy of the first molecule; (c) repeating steps (a)–(b) for the second molecule; and (d) comparing the conformational free energy of the first molecule with the conformational free energy of the second molecule and determining which molecule has lower conformational free energy thereby determining which molecule is more stable.

DETAILED DESCRIPTION OF THE INVENTION

Figure 4:
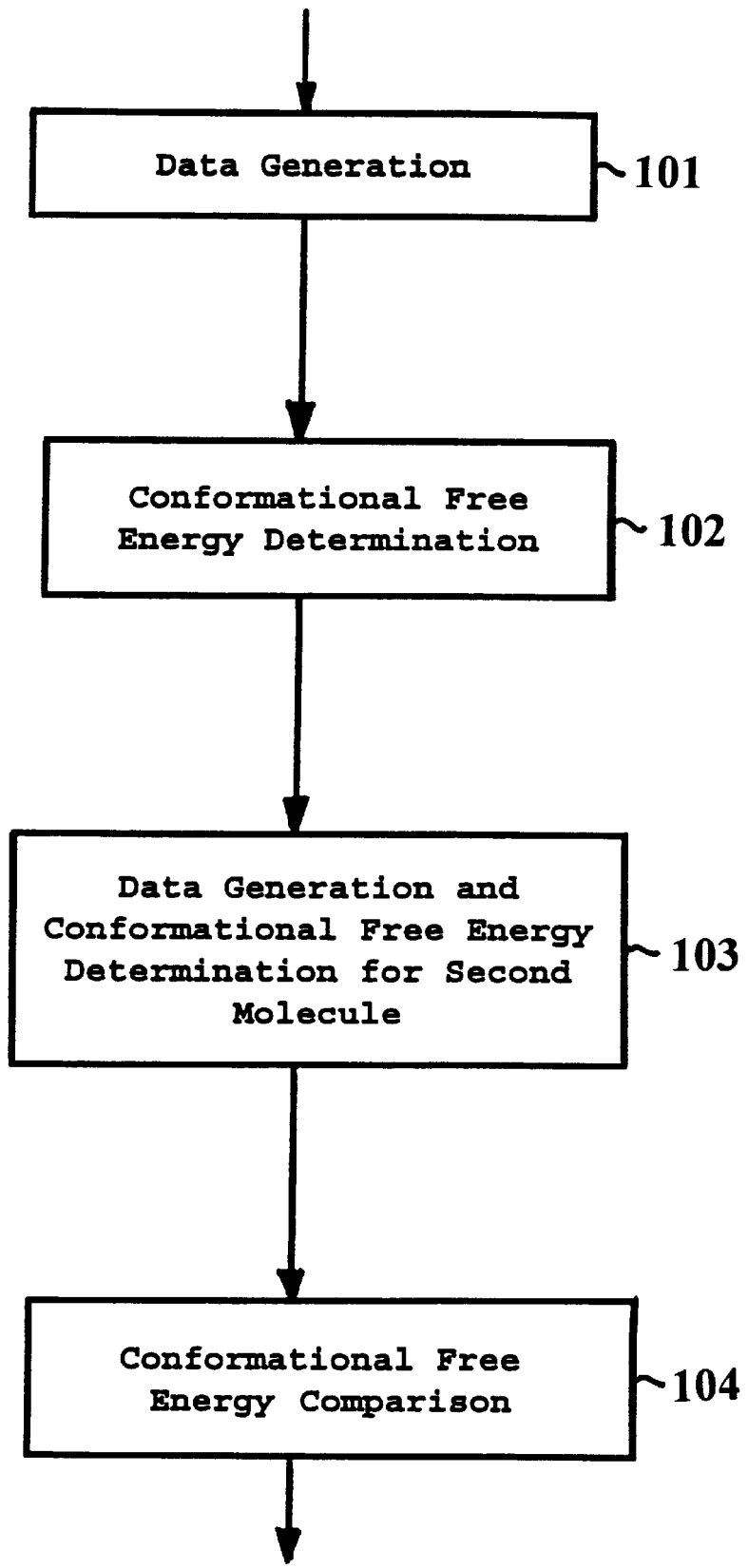
FIG. 4 shows a flow chart of a method of one embodiment of the present invention.

The invention is directed to a method, as shown in FIG. 4, of using a computer processor to analyze electrical signals and data representative of a first molecule to determine conformational free energy of the first molecule so as to determine whether the first molecule is more stable than a second molecule, wherein both molecules have a predefined connectivity and exist in a predefined environment, comprising:

(a) step 101 including generating a set of data representative of low-energy minimum conformations of the first molecule derived from connectivity of the first molecule, a potential energy function, and a conformational search method;

(b) step 102 including determining conformational free energy of the first molecule by calculating a configuration integral in all degrees of freedom based upon a contribution of each conformation of the set of conformations of the first molecule, wherein the configuration integral is calculated by:

(i) performing importance sampling multidimensional Monte Carlo integration over a multidimensional volume enclosing a current conformation of the first molecule in a conformational space, wherein the volume is dependent on harmonic vibrational frequencies of the current conformation and temperature, wherein the importance sampling comprises preferentially sampling regions of the volume in conformational space associated with the current conformation which regions have dominant contribution to the conformational free energy of the current conformation, and wherein the importance sampling utilizes a physical background consisting essentially of normal modes of vibration of the first molecule and the sampling is performed using an atomic coordinate transformation which is based on eigenvectors of a Hessian matrix associated with the current conformation;

(ii) repeating step (i) for each conformation in the set of data; and (iii) summing the conformational contributions determined in steps (i–ii) so as to determine a total configuration integral for the first molecule and thereby determine the conformational free energy of the first molecule;

(c) step 103 including repeating steps (a)–(b) for the second molecule; and (d) step 104 including comparing the conformational free energy of the first molecule with the conformational free energy of the second molecule and determining which molecule has lower conformational free energy thereby determining which molecule is more stable.

The low-energy minimum conformations may be up to about 15 kiloJoules per mole to about 35 kiloJoules per mole with respect to a lowest energy conformation. The potential energy function may be based on molecular mechanics, semi-empirical quantum mechanics, ab initio quantum mechanics or density functional quantum mechanics.

The atomic coordinates may comprise internal atomic coordinates or external atomic coordinates. The external atomic coordinates may comprise Cartesian coordinates. The internal atomic coordinates may comprise bond lengths, bond angles, or torsional angles. The Hessian matrix may comprise an exact Hessian matrix or an approximation of an exact Hessian matrix.

In one embodiment, the first molecule may comprise a molecular complex. In another embodiment, the second molecule may comprise a molecular complex. The environment may comprise presence of solvent, a vacuum, or presence of a third molecule, or any number of subsequent molecules.

In one embodiment of the present invention, the first molecule or the second molecule or both molecules may be subjected to extrinsic forces from the environment.

The first molecule may comprise a cyclic or an acyclic molecule. The second molecule may comprise a cyclic or an acyclic molecule. The first molecule and the second molecule may move with respect to one another.

The first molecule may comprise water, a biopolymer, a bio-oligomer, a protein, an enzyme, a peptide, a nucleic acid, a carbohydrate, a glycoprotein, a receptor, a lipid bilayer, a bio-compatible polymer, a metal, an organic compound, an inorganic compound, a natural product, a pharmaceutical compound, a drug or a drug candidate.

The second molecule or the third molecule or any subsequent molecule may comprise water, a biopolymer, a bio-oligomer, a protein, an enzyme, a peptide, a nucleic acid, a carbohydrate, a glycoprotein, a receptor, a lipid bilayer, a bio-compatible polymer, a metal, an organic compound, an inorganic compound, a natural product, a pharmaceutical compound, a drug or a drug candidate.

In one embodiment of the present invention, the method is used to select a drug candidate.

Figure 5:
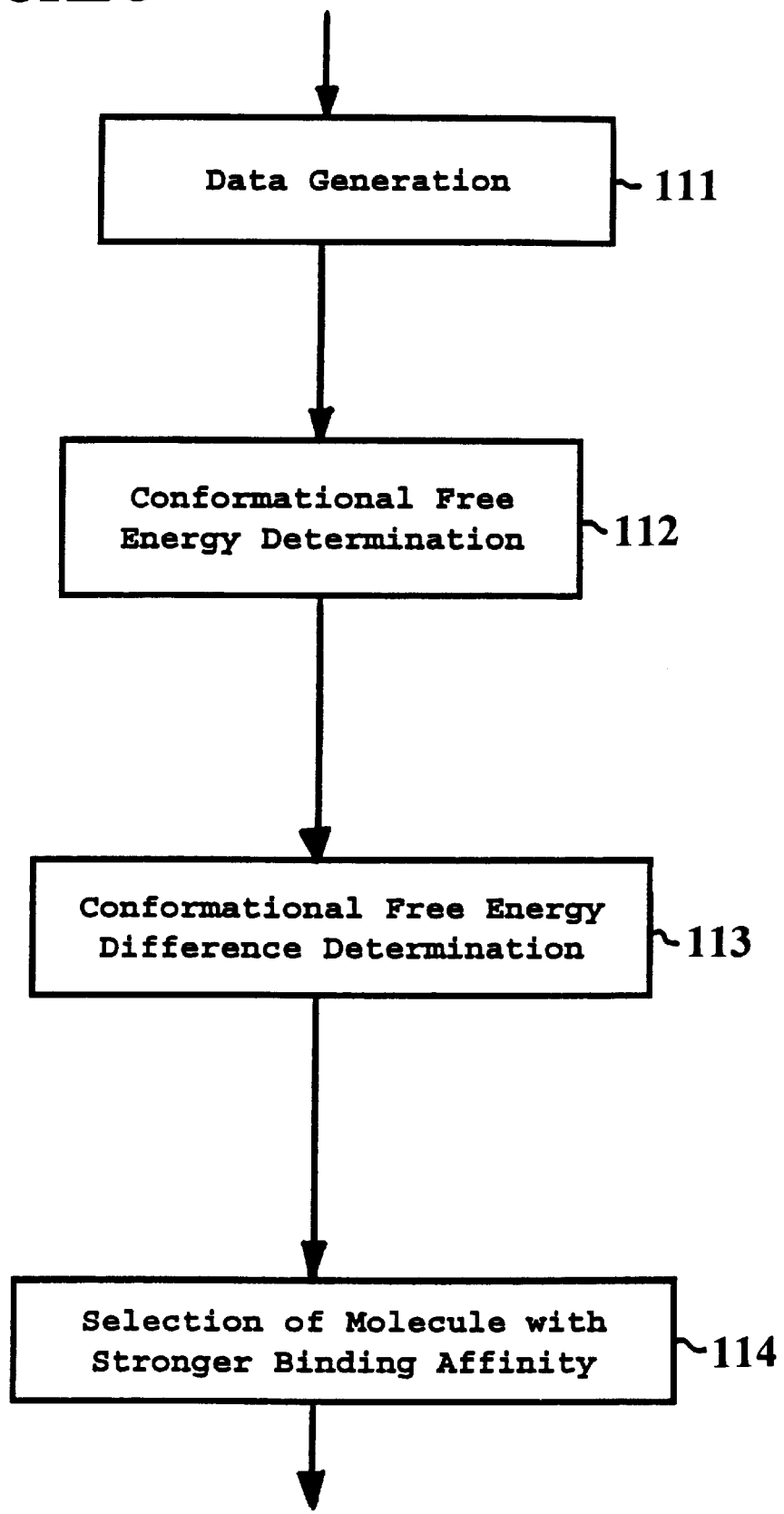
FIG. 5 shows a flow chart of a method of another embodiment of the present invention.

The present invention also provides for a method, as shown in FIG. 5, of using a computer processor to analyze electrical signals and data representative of conformations of molecular complexes to select either a first molecule or a second molecule as the molecule with stronger binding affinity to a host molecule, wherein the molecules have predefined connectivities and exist in a predefined environment, comprising:

(a) step 111 including generating four sets of data representative of low-energy minimum conformations of:

(1) the first molecule,
(2) the first molecular complex comprising the first molecule bound to the host molecule,
(3) the second molecule, and
(4) the second molecular complex comprising the second molecule bound to the host molecule, wherein each set of data is derived from:

(i) connectivity of the molecule or the molecular complex,
(ii) a potential energy function, and
(iii) a conformational search method;

(b) step 112 including determining conformational free energy of each set by calculating a configuration integral in all degrees of freedom based upon a contribution of each conformation of the set of conformations, wherein the configuration integral is calculated by:

(i) performing importance sampling multidimensional Monte Carlo integration over a multidimensional volume enclosing a current conformation in a conformational space, wherein the volume is dependent on harmonic vibrational frequencies of the current conformation and temperature, wherein the importance sampling comprises preferentially sampling regions of the volume in conformational space associated with the current conformation which regions have dominant contribution to the conformational free energy of the current conformation, and wherein the importance sampling utilizes a physical background consisting essentially of normal modes of vibration and is performed using an atomic coordinate transformation which is based on eigenvectors of a Hessian matrix associated with the current conformation;

(ii) repeating step (i) for each conformation in each set; and (iii) summing the conformational contributions determined in steps (i–ii) separately for each set so as to determine a total configuration integral and thereby determining a value representative of conformation free energy of the first molecule, the first molecular complex, the second molecule and the second molecular complex;

(c) step 113 including calculating the difference between the conformational free energy value for the second molecule and the value for the first molecule and the difference between the value for the second molecular complex and the value of the first molecular complex, and subtracting the difference between the molecules from the difference between the molecular complexes so as to determine a total difference;

(d) step 114 including determining the sign of the total difference calculated in step (c) and selecting the first molecule if the difference is negative or selecting the second molecule if the difference is positive so as to select the molecule with stronger binding affinity to the host molecule.

In one embodiment, the method is repeated and a third molecule and a third molecular complex is substituted for the molecule and molecular complex which is not selected after the first performance of the method.

The low-energy minimum conformations may be up to about 15 kiloJoules per mole to about 35 kiloJoules per mole with respect to a lowest energy conformation.

The potential energy function may be based on molecular mechanics, semi-empirical quantum mechanics, ab initio quantum mechanics or density functional quantum mechanics. The atomic coordinates may comprise internal atomic coordinates or external atomic coordinates. The external atomic coordinates may comprise Cartesian coordinates. The internal atomic coordinates may comprise bond lengths, bond angles, torsional angles or relative spatial position of members of each molecular complex defined by three translational and three rotational degrees of freedom. The Hessian matrix may comprise an exact Hessian matrix or an approximation of an exact Hessian matrix. The environment may comprise presence of solvent, a vacuum, or presence of a third molecule. In another embodiment, the molecules or the molecular complexes may be subjected to extrinsic forces from the environment.

In another embodiment, the first molecule comprises a cyclic or an acyclic molecule. The second molecule may comprise a cyclic or an acyclic molecule. The host molecule may comprise a cyclic or an acyclic molecule. In a further embodiment, the first molecule or the second molecule, and the host molecule may move with respect to one another.

The first molecule may comprise water, a biopolymer, a bio-oligomer, a protein, an enzyme, a peptide, a nucleic acid, a carbohydrate, a glycoprotein, a receptor, a lipid bilayer, a bio-compatible polymer, a metal, an organic compound, an inorganic compound, a natural product, a pharmaceutical compound, a drug or a drug candidate.

The second molecule may comprises water, a biopolymer, a bio-oligomer, a protein, an enzyme, a peptide, a nucleic acid, a carbohydrate, a glycoprotein, a receptor, a lipid bilayer, a bio-compatible polymer, a metal, an organic compound, an inorganic compound, a natural product, a pharmaceutical compound, a drug or a drug candidate.

The host molecule may comprise water, a biopolymer, a bio-oligomer, a protein, an enzyme, a peptide, a nucleic acid, a carbohydrate, a glycoprotein, a receptor, a lipid bilayer, a bio-compatible polymer, a metal, an organic compound, an inorganic compound, a natural product, a pharmaceutical compound, a drug or a drug candidate.

In one embodiment, the method is used to select a drug candidate.

Figure 6:
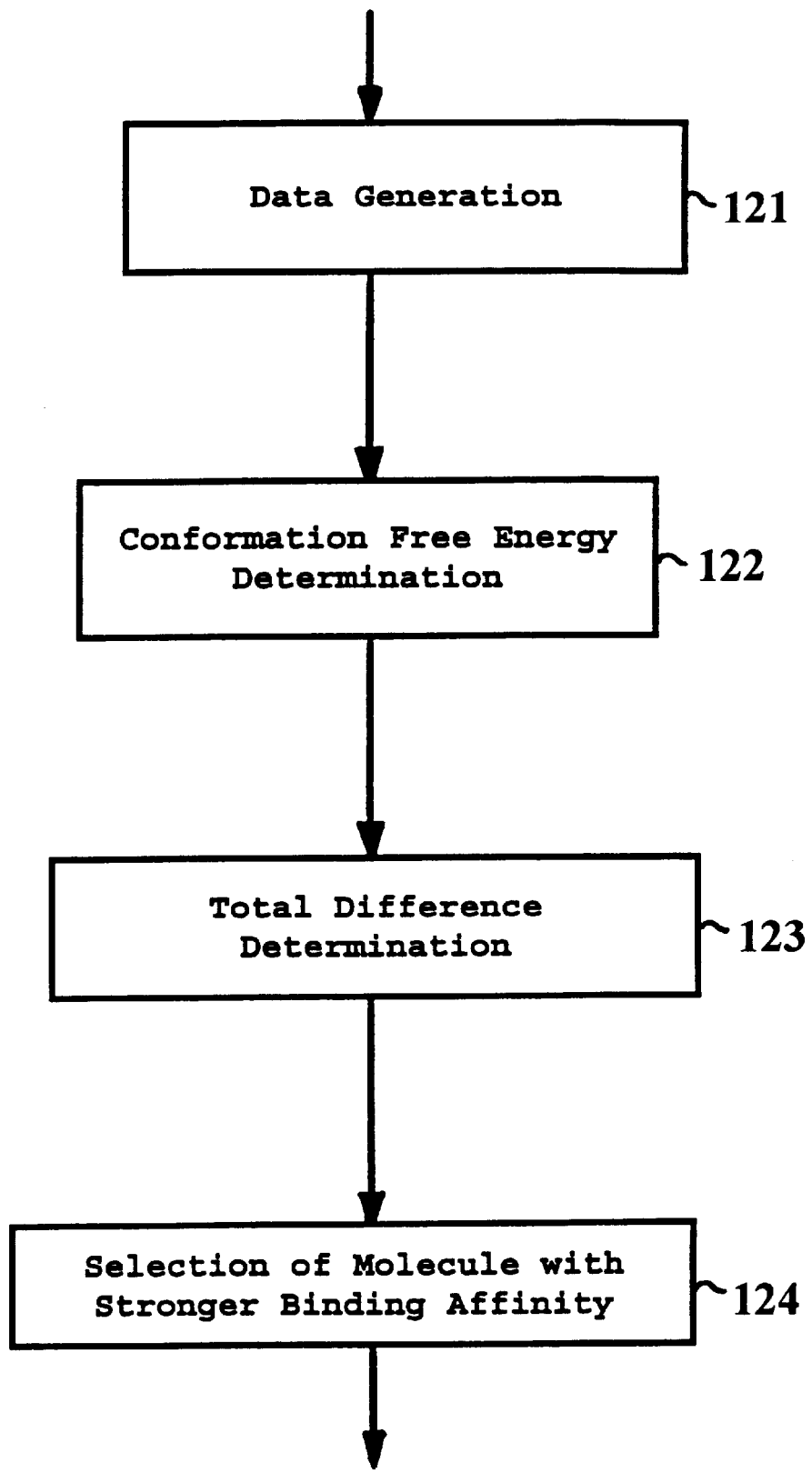
FIG. 6 shows a flow chart of a method of a third embodiment of the present invention.

The present invention also provides a method, as shown in FIG. 6, of using a computer processor to analyze electrical signals and data representative of conformations of molecular complexes to select either a first molecule or a second molecule as the molecule with stronger binding affinity to a host molecule, wherein the first and second molecules are stereoisomers and exist in a predefined environment, comprising:

(a) step 121 including generating two sets of data representative of low-energy minimum conformations of:

(1) the first molecular complex comprising the first molecule bound to the host molecule, and (2) the second molecular complex comprising the second molecule bound to the host molecule, wherein each set of data is derived from:

(i) connectivity of the molecular complex, (ii) a potential energy function, and (iii) a conformational search method;

(b) step 122 including determining conformational free energy of each set by calculating a configuration integral in all degrees of freedom based upon a contribution of each conformation of the set of conformations, wherein the configuration integral is calculated by:

(i) performing importance sampling multidimensional Monte Carlo integration over a multidimensional volume enclosing a current conformation in a conformational space, wherein the volume is dependent on harmonic vibrational frequencies of the current conformation and temperature, wherein the importance sampling comprises preferentially sampling regions of the volume in conformational space associated with the current conformation which regions have dominant contribution to the conformational free energy of the current conformation, and wherein the importance sampling utilizes a physical background consisting essentially of normal modes of vibration and the sampling is performed using an atomic coordinate transformation which is based on eigenvectors of a Hessian matrix associated with the current conformation;

(ii) repeating step (i) for each conformation in each set; and (iii) summing the conformational contributions determined in steps (i–ii) separately for each set so as to determine a total configuration integral and thereby determining a value representative of conformation free energy of the first first molecular complex, and the second molecular complex;

(c) step 123 including calculating the difference between the value for the second molecular complex and the value of the first molecular complex so as to determine a total difference;

(d) step 124 including determining the sign of the total difference calculated in step (c) and selecting the first molecule if the difference is negative or selecting the second molecule if the difference is positive so as to select the molecule with stronger binding affinity to the host molecule.

Figure 7:
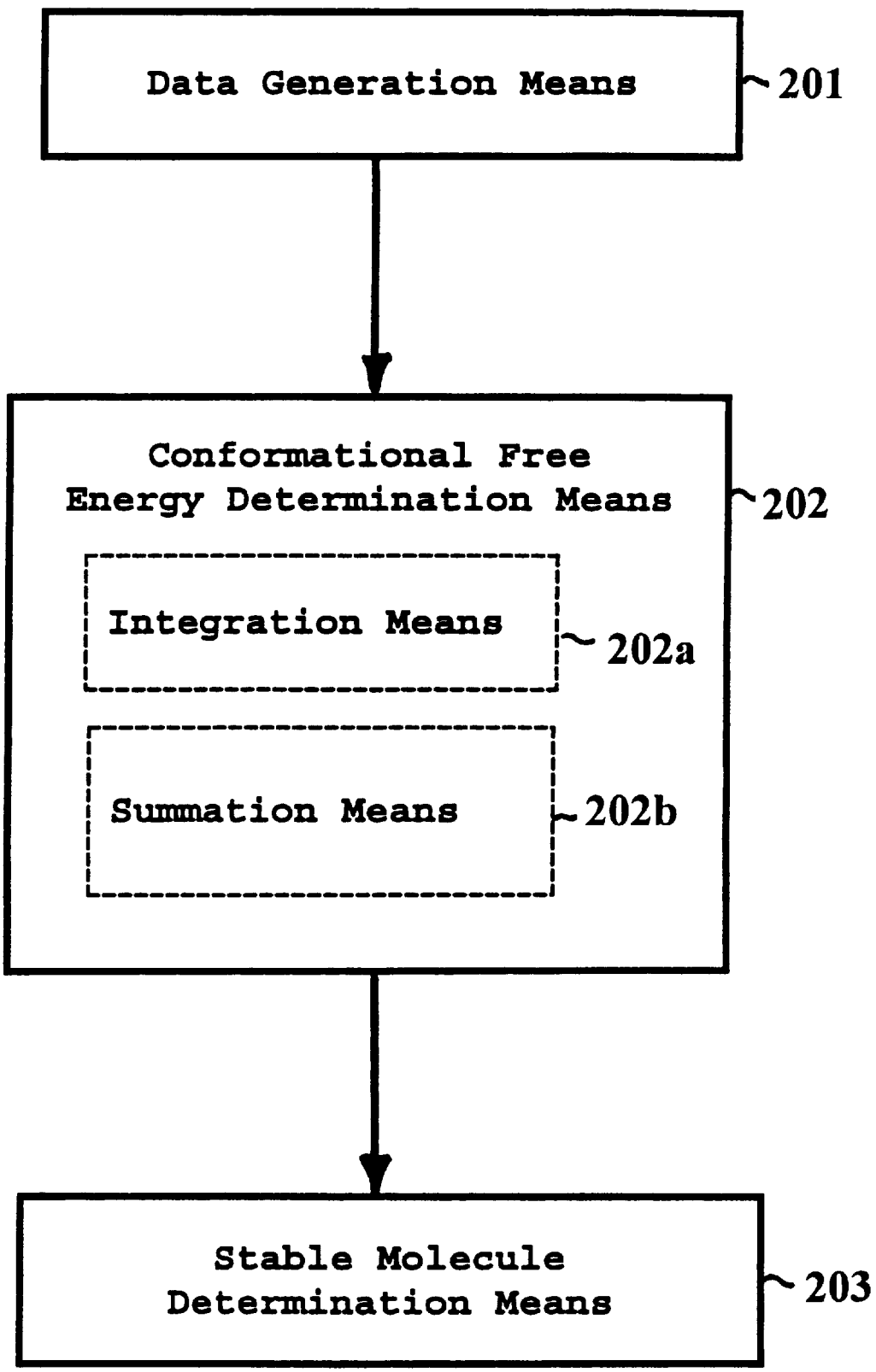
FIG. 7 shows a schematic drawing of an apparatus of one embodiment of the present invention.

The present invention also provides for an apparatus, as shown in FIG. 7, capable of analyzing electrical signals and data representative of a first molecule to determine conformational free energy of the first molecule so as to determine whether a first molecule is more stable than a second molecule, wherein both molecules exist in a predefined environment, comprising:

(a) means 201 for generating a set of data representative of low-energy minimum conformations of the first molecule derived from connectivity of the first molecule, a potential energy function, and a conformational search method;

(b) means 202 for determining conformational free energy of the first molecule by calculating a configuration integral in all degrees of freedom based upon a contribution of each conformation of the set of conformations of the first molecule, wherein the configuration integral is calculated by:

(i) 202a means for performing importance sampling multidimensional Monte Carlo integration over a multidimensional volume enclosing a current conformation of the first molecule in a conformational space, wherein the volume is dependent on harmonic vibrational frequencies of the current conformation and temperature, wherein the importance sampling comprises preferentially sampling regions of the volume in conformational space associated with the current conformation which regions have dominant contribution to the conformational free energy of the current conformation, and wherein the importance sampling utilizes a physical background consisting essentially of normal modes of vibration of the first molecule and the sampling is performed using an atomic coordinate transformation which is based on eigenvectors of a Hessian matrix associated with the current conformation;

(ii) means 202a for repeating step (i) for each conformation in the set; and (iii) means 202b for summing the conformational contributions determined in steps (i–ii) so as to determine a total configuration integral for the first molecule and thereby determine the conformational free energy of the first molecule;

(c) means 201 and 202 for repeating steps (a)–(b) for the second molecule; and (d) means 203 for comparing the conformational free energy of the first molecule with the conformational free energy of the second molecule and determining which molecule has lower conformational free energy thereby determining which molecule is more stable.

Figure 8:
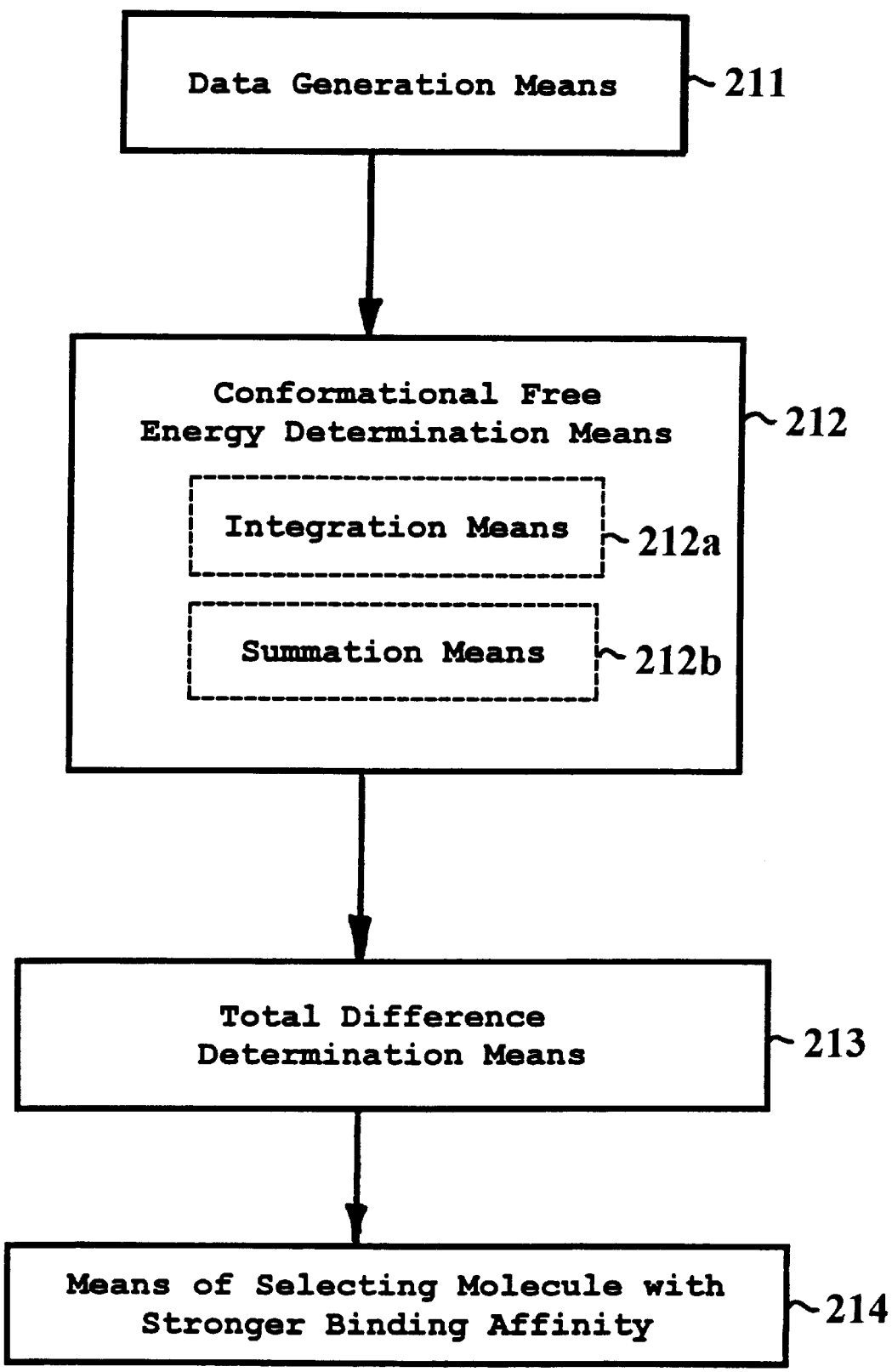
FIG. 8 shows a schematic drawing of an apparatus of another embodiment of the present invention.

The present invention provides for an apparatus, as shown in FIG. 8, capable of analyzing electrical signals and data representative of conformations of molecular complexes to select either a first molecule or a second molecule as the molecule with stronger binding affinity to a host molecule, wherein the molecules have predefined connectivities and exist in a predefined environment, comprising:

(a) means 211 for generating four sets of data representative of low-energy minimum conformations of:
(1) the first molecule,
(2) the first molecular complex comprising the first molecule bound to the host molecule,
(3) the second molecule, and
(4) the second molecular complex comprising the second molecule bound to the host molecule, wherein each set of data is derived from:

(i) connectivity of the molecule or the molecular complex,
(ii) a potential energy function, and
(iii) a conformational search method;

(b) means 212 for determining conformational free energy of each set by calculating a configuration integral in all degrees of freedom based upon a contribution of each conformation of the set of conformations, wherein the configuration integral is calculated by:

(i) means 212a for performing importance sampling multidimensional Monte Carlo integration over a multidimensional volume enclosing a current conformation in a conformational space, wherein the volume is dependent on harmonic vibrational frequencies of the current conformation and temperature, wherein the importance sampling comprises preferentially sampling regions of the volume in conformational space associated with the current conformation which regions have dominant contribution to the conformational free energy of the current conformation, and wherein the importance sampling utilizes a physical background consisting essentially of normal modes of vibration and is performed using an atomic coordinate transformation which is based on eigenvectors of a Hessian matrix associated with the current conformation;

(ii) means 212a for repeating step (i) for each conformation in each set; and (iii) means 212b for summing the conformational contributions determined in steps (i–ii) separately for each set so as to determine a total configuration integral and thereby determining a value representative of conformation free energy of the first molecule, the first molecular complex, the second molecule and the second molecular complex;

(c) means 213 for calculating the difference between the conformational free energy value for the second molecule and the value for the first molecule and the difference between the value for the second molecular complex and the value of the first molecular complex, and subtracting the difference between the molecules from the difference between the molecular complexes so as to determine a total difference;

$$\Delta\Delta G = \{[CFE_{L1-H} - CFE_{L1}] - [CFE_{L2-H} - CFE_{L2}]\}$$

(d) means 214 for determining the sign of the total difference calculated in step (c) and selecting the first molecule if the difference is negative or selecting the second molecule if the difference is positive so as to select the molecule with stronger binding affinity to the host molecule.

The present invention also provides a method as described hereinabove wherein the calculation is not the relative binding free energy but rather the absolute binding free energy. In one embodiment, a calculation is carried out taking the difference as shown:

$$\Delta\Delta G = \{[CFE_{L1-H} - (CFE_{L1} + CFE_H)] - [CFE_{L2-H} - (CFE_{L2} + CFE_H)]\}$$

As used herein "connectivity" of a molecule is encompassed by the definition of the atom types of the molecule and the network of chemical bonds that hold the atom types together.

The conformation of the molecule or molecular complex may be stored in computer readable form.

Hardware suitable for carrying out the methods could include any fast digital processor. In particular, UNIX workstations (Silicon Graphics CHALLENGE, $O_2$, OCTANE, IRIS, INDIGO, INDIGO$^2$; IBM RS/6000; Hewlett Packard Model 9000) and supercomputers (e.g. CRAY Y-MP; IBM SM1 and SM2) would be particularly suitable. For graphical display of results, IBM RS/6000 and Silicon Graphics IRIS, INDIGO or INDIGO$^2$ graphics workstations can be used.

During the past three decades modern biology has come to recognize the importance of the three-dimensional conformation/shape of biological molecules in relation to the observed function and activity of these molecules. Beginning with the first identification of alpha helical structures in proteins through the solution to the structure of DNA as a hydrogen bonded intertwined double helix to current studies by X-ray crystallography of enzyme-substrate complexes, appreciation of the role of shape as a determining factor has continually increased.

In fact, it is now understood that a proper description and understanding of the functioning of most biological macromolecules is dependent on an understanding of the three-dimensional shape of the molecules. The situation is often analogized to that of a three-dimensional jigsaw puzzle, where the parts which must fit together interlock in specific patterns in three dimensions. It is now realized that the binding of a molecular substrate to an enzyme is determined by the ability of the substrate to fit a notch/groove/cavity within the enzyme in such a manner that the substrate is both mechanically and chemically stabilized in the correct three-dimensional and thermodynamic orientation to promote the catalytic reaction. Similarly, it has long been recognized that the highly specific binding of antibodies to antigens is accomplished by the recognition by the antibody of the surface shape specific features of the antigen molecule.

Not only is the understanding of these three-dimensional puzzles important to a fundamental understanding of enzymology, immunology, and biochemistry, but such studies are of major interest to therapeutic drug researchers. Most drug effects are accomplished by the binding of a drug to a target receptor molecule. To the extent that the nature of the binding is more fully understood, it should be possible to design drugs which bind to their target molecules with greater precision and effect than even naturally occurring compounds. This therapeutic quest is especially important in cancer research where the generalized side effects of many therapeutic drugs are undesirable and more specific drug interactions are desired.

Along with the recognition of the importance of the three-dimensional stereo conformation of biomolecules has come an appreciation of just how difficult it is to understand how the conformation of the molecules is related to their activity. At the present time, the only known method for determining exactly the three-dimensional shape of any biomolecule is by means of X-ray crystallography. While the number of biomolecules which have had their structure successfully determined by crystallography is growing rapidly, the total number remains relatively small, and an even fewer number have been studied in crystal form in conjunction with their bound substrates or ligands. Of the few ligand-biomolecule combinations which have been successfully analyzed by X-ray crystallography, there is still the open question as to whether the complex exists in a different conformational combination in solution than it does in the crystallized form used for the study, although the evidence suggests that there is no major difference.

For the present invention, the SYBYL program of Tripos® Associates, Inc. may be utilized. There are several other programs available which are functionally equivalent and may be used with the present invention. Examples are:

MacroModel®—from Columbia Univ.

ChemX®—from Chemical Design LTD., Oxford, UK

Insight®—from BioSym Technologies, San Diego, Calif.

Quanta®—from Polygen, Waltham, Mass.

ChemLab®—from Molecular Design Ltd., San Leandro, Calif.

Such a host program must support the building and storage of molecular models (retrieval of the atomic coordinates) plus the calculation of atomic charges (for electrostatic field computation) and the tabulation of steric parameters by atomic type (for steric field computation) Such programs should be capable of applying a Potential Energy Function and be able to calculate a gradient and Hessian matrix of the Potential Energy Function.

This invention is illustrated in the Experimental Details section which follows. These sections are set forth to aid in an understanding of the invention but are not intended to, and should not be construed to, limit in any way the invention as set forth in the claims which follow thereafter.

EXPERIMENTAL DETAILS

EXAMPLE 1

Evaluation of the Molecular Configuration Integral in All Degrees of Freedom for the Direct Calculation of Conformational Free Energies: Prediction of the Anomeric Free Energy of Monosaccharides A novel theoretical approach is presented for the direct calculation of conformational free energies without the need for expensive free energy simulations and the use of computational alchemy. It is shown that conformational search combined with advanced Monte Carlo integration can tackle the daunting problem of solving the molecular configuration integral in all degrees of freedom, affording a direct method to calculate accurate conformational free energies. The new algorithm termed mode integration (MINTA) was applied here to explain anharmonic effects in cycloheptane, and to predict the A value of cyclohexane derivatives and the anomeric free energy of carbohydrates (tertrahydropyran derivatives and pyranose monosaccharides) using a continuum solvation model.

Chemical stability can always be formulated in terms of conformational free energy (CFE) differences. There can be various levels envisioned at which approximations to CFE differences can be made. For example, if one wishes to calculate the anomeric free energy for the equilibrium of $\alpha$ and $\beta$ anomers of monosaccharides, then the simplest approach one can follow is to calculate the energy difference between the lowest energy $\alpha$ and the lowest energy $\beta$ anomer. Of course, this approach ignores entropic effects due to the fact that first of all there are multiple conformations of both the $\alpha$ and $\beta$ anomers and second of all, the individual conformations are not static (confined to the bottom of their energy well) but exhibit large dynamic diversity in terms of conformational changes limited to that energy well. Note that glucose, for example, possesses literally hundreds of low-energy conformations of both anomeric states.

The next level of approximation to the CFE is the inclusion of multiple conformations. With this model, two families of different conformational-, configurational- or stereoisomers, both represented by multiple conformations, are considered as two sets of discrete energy levels corresponding to the energies of the individual conformations. A simple statistical mechanics calculation can then be used to estimate the free energy difference between the two families. Note that such families, henceforth termed somewhat confusingly conformational families, can represent either multiple conformations related to each other by some geometrical criterion such as holding axial or equatorial substituents, or multiple conformations of stereoisomers. The terms conformational free energy and conformational free energy difference are used generally throughout. However, e.g., the A values of cyclohexane derivatives (vide infra) represent actual conformational free energy differences, but the anomeric free energy of monosaccharides refers to the free energy difference between α and β diastereosomers, i.e., α,β anomers.

The ultimate approach for calculating the free energy difference ΔG between two conformational families, in the classical sense, involves the evaluation of the molecular configuration integral Q:

$$Q_1 = \sum_{i=1}^{n_1} \int_{V_i^1} e^{-\frac{E(r)-E_0}{RT}} dr,$$ (Equation 1)

$$Q_2 = \sum_{i=1}^{n_2} \int_{V_i^2} e^{-\frac{E(r)-E_0}{RT}} dr$$

$$\Delta G_{12} = -RT \ln \frac{Q_1}{Q_2} = -RT \ln K_{12}$$ (Equation 2)

where the indices 1 and 2 refer to two conformational families. It is assumed throughout that the dominant part of the configuration integral comes from contribution at or near to low-energy conformations. Therefore, Q is summed over, respectively, $n_1$ and $n_2$ conformations each encompassing different V volumes of the conformational space. E(r) is the molecular mechanics energy with respect to the nuclear coordinates r. $E_0$ is the global minimum energy which is the common reference for both conformational families. R is the gas constant and T is the absolute temperature. $K_{12}$ in the second term of equation (2) is the population ratio of the conformational families at equilibrium. Note that all of the symmetry related copies of a single conformation included in the sum in equation (1) to account for the statistical correction for conformational symmetry.

Direct evaluation of the configuration integral has been considered to be impossible to solve except for problems of very low dimensionality. Instead, indirect methods utilizing various simulation techniques based on free energy perturbation (FEP) (Kollman, 1993) and recently, a novel smart Monte Carlo approach termed jump-between-wells (JBW) (Senderowitz et al., 1995) have been used extensively to calculate conformational free energy differences. The JBW method coupled with molecular dynamics involves directly monitoring the populations of various conformations of the two conformational families (rhs. of eq 2) in a simulation in which conformational interconversions occur frequently, producing converged, Boltzmann-weighted ensembles of conformational states.

Very recently, direct methods have also emerged that involve the direct evaluation of the configuration integral as sums over conformational minima (equation 1). Most notably, a new method termed "mining minima" has been introduced in which the configuration integral is evaluated over the "soft modes" identified as torsion angles (Head et al., 1997). It should be stressed, however, that the exclusion of "hard modes" such as bond lengths and bond angles is, in general, a poor approximation. Cyclic structures, e.g., undergo sufficient variation of their ring bond angles and even bond lengths during conformational interconversions, to contribute a significant amount to the conformational free energy. Therefore, a method is sought that can evaluate the configuration integral in all degrees of freedom, in order to calculate accurate free energies.

The "mining minima" method could, in principle, include the hard modes, but in practice, it is limited to only a few degrees of freedom, because it is based on simple Monte Carlo integration. The evaluation of multidimensional integrals is a daunting task and for dimensions>3, Monte Carlo integration is the only method available. However, simple Monte Carlo integration requires a vast number of function evaluations to afford reasonably accurate integrals when more than about half a dozen dimensions are considered (Stroud et al., 1971; Lepage, 1978; Press et al., 1992). A novel Monte Carlo integration technique is presented herein, termed mode integration (MINTA) that operates in all degrees of freedom. The new method allows, for the first time, for the direct calculation of conformational free energies of diverse systems, and gives results that are virtually identical with those obtained by converged JBW simulations. The MINTA method is applied here to predict the A value of cyclohexane derivatives and the anomeric free energy of carbohydrates (tertrahydropyran derivatives and pyranose monosaccharides) using a continuum solvation model.

Conformational Search. Mode integration relies upon an exhaustive conformational search of the low-energy minima. The method of choice as set forth herein is a particularly efficient conformational search procedure termed low-mode conformational search (LMOD) (Kolossváry, 1996)

Monte Carlo Integration. Mode integration is based on a novel use of the harmonic approximation to achieve remarkable accuracy in the numerical integration of high-dimensional molecular configuration integrals. Importance sampling Monte Carlo integration utilizes a sampling function to preferentially sample the integrand in those regions where the integrand has a significant magnitude. The basic theorem of importance sampling Monte Carlo integration asserts that the optimal choice of the sampling function p for the numerical integration of a function f (in any dimensions) is p |f|, i.e., the more one knows about f the better one can estimate ∫f (Press et al., 1992). The basic tenet of mode integration is to construct a sampling function which is very similar to the partition function (eq 1), in the vicinity of low-energy minima on the PES.

The obvious approach is to apply the harmonic approximation to each low-energy well on the PES by a local, second order Taylor expansion of the potential energy function (Karplus et al., 1981; Levy et al., 1984). The resulting sampling functions are normalized multivariate Gaussians $$P_i = \sqrt{\frac{\det H_i}{(2\pi RT)^n}} \exp\left(-\frac{1}{2RT}(r-r_i)H_i(r-r_i)\right)$$ (Equation 3)

where $r_i$ and $H_i$ denote, respectively, the bottom of a particular energy well and the associated local Hessian matrix. The Hessian is evaluated at the bottom of the well, The number of degrees of freedom n is equal to the number of unconstrained internal coordinates. Note that $p_i$ also depends on the temperature via RT.

Mode integration means, in essence, that eq 3 is utilized as a sampling function to integrate eq 1. However, for the reduction of the proposed theory in practice, one needs to consider two important issues: definition on the volume that is associated with a particular conformation in conformational space and to find an optimal coordinate system that guarantees the most accurate integral estimates. The optimal coordinate system can be derived by considering a simple fact about multivariate Gaussians. In real Gaussians, H is essentially the inverse of the covariance matrix which accounts for the correlation between the random variables of the multivariate Gaussian distribution. Unless the covariance matrix is diagonal, the off-diagonal elements give rise to mixed terms in the Gaussian exponential. However, by suitable coordinate transformation termed prinicple component transformation, which is based on the diagonalization of the covariance matrix, the mixed terms can always be eliminated. The resulting Gaussian can be expressed as a product of n independent, univariate Gaussian functions. Analogously, a similar transformation can be applied to the Hessian matrix. The eigenvectors of the Hessian matrix $H_i$ span a local, orthogonal coordinate system centered at $r_i$, which is closely related to the normal modes of vibration. Utilizing the eigenvectors of the Hessian matrix in eq 3 results in a sampling function that can be expressed as a product of an independent, univariate Gaussian functions whose single variable represents the corresponding normal mode. Importance sampling based on the proposed, separable sampling function involves consecutively sampling n independent, one-dimensional Gaussian functions.

The normal mode coordinate system also provides a simple definition of the integration volume. The tail-off of one-dimensional Gaussians can be measured conveniently in units of standard deviation ($\sigma$). Approximately 68% of the underlying population is covered by $\pm\sigma$, and 99.7% by $\pm 3\sigma$. In terms of a Gaussian partition function, this means that beyond three-four standard deviations the Boltzmann probability vanishes. Thus, the proposed multidimensional integration volume is a n-dimensional hypercube which is aligned along the normal modes, and whose dimensions depend on the harmonic vibrational frequencies as well as the temperature. Note that the integration volume is different for different conformations. MINTA therefore, utilizes the following separable sampling function for the Monte Carlo integration of the molecular configuration integral:

$$P_i = \prod_j^n \sqrt{\frac{\lambda_j}{2\pi RT}} \exp\left(-\frac{\lambda_j x_j^2}{2RT}\right) \quad \text{(Equation 4)}$$

where j=1 ... n normal modes, $\lambda_1 \ldots \lambda_n$ are the eigenvalues of the non-mass-weighted Hessian matrix, and $x_1 \ldots x_n$ are the corresponding normal coordinates represented by the eigenvectors of the Hessian matrix. The center of the normal coordinate system is located at the bottom of the energy well where the gradient of the potential energy vanishes. $\sqrt{(RT/\lambda_j)}$ represents the quasi standard deviation of the Gaussian. Note that eq 4 refers to a single conformation i. Mode integration of the full molecular configuration integral involves integrating the individual, conformational partition functions via importance sampling using eq 4, and summing them up (eq 1):

$$Q = \sum_i^{n_{conf}} S_i \int_{\square_i} \left(\frac{e^{-\frac{E(x_i)-E_{0i}}{RT}}}{p_i}\right) p_i dx_i \quad \text{(Equation 5)}$$

-continued
$$\approx \sum_i^{n_{conf}} S_i \left\langle \frac{e^{-\frac{E(x_i)-E_{0i}}{RT}}}{p_i} \right\rangle_{\square_i}$$

where $p_i$ is the Gaussian sampling function (eq 4), $x_i$ is the vector of normal coordinates and $s_i$ is the symmetry number, of conformation i. The < > brackets indicate averaging. The integration volume $\square_i$ is a n-dimensional hypercube with dimensions $d_j=2$ const $\sqrt{(RT/\lambda_j)}$ measured in units of the quasi standard deviation (eq 4), j=1 ... n and const is a multiplication factor. Note that in eq 5 $E_{0i}$, the reference for the energy difference in the Boltzmann exponential is the bottom of the individual energy wells, not the global minimum, $E_0$ (eq 1). Of course, this is only a matter of scaling. The right hand side of eq 5 is utilized to estimate the configuration integral by importance sampling inside the multidimensional hypercubes.

The essence of mode integration can be captured in a single sentence: The underlying idea that makes the method work is a novel use of the harmonic approximation for the particularly effective importance sampling of the true potential energy surface in the framework of multidimensional Monte Carlo integration.

Computational Details

The low-mode conformational search procedure and the MINTA method have been integrated into the MacroModel/Batchmin computational chemistry program package (Mohamadi et al., 1990). The calculations have been carried out using version 5.5 of Batchmin running on Silicon Graphics workstations.

Integration volume. Preliminary calculations were aimed at defining the size of the hypercubes in eq 5. Note that due to possibly overlapping hypercubes, double sampling can, in principle, give rise to biased integral estimates. Randomly selected conformations of several cycloalkanes and monosaccharides were subjected to test calculations with variable size hypercubes ranging from 1 to 5 standard deviations. The results clearly showed that the intuitive choice of $3\sigma$ was generally applicable to give converged free energies. Furthermore, it was shown that the overlap issue was negligible except for one notable case, the twist-boat (TB) conformation of cycloheptane which is discussed further below. For all other cases, a simple test showed that the $3\sigma$ hypercubes did not extend beyond the catchment region of their associated conformation. In this test calculation, thousands of structures generated by the Monte Carlo sampling were all saved and re-minimized to see whether sampling had escaped from the minimum well. Using $3\sigma$, none of the trial structures crossed a conformational barrier during re-minimization. Even using $4\sigma$ and $5\sigma$ afforded only a very few cases where re-minimization of a trial structure carried it over to a different conformational minimum. Therefore, it was concluded that the integration volumes (eq 5) should be defined as $3\sigma$ hypercubes throughout.

Results and Discussion

Anharmonic effects in cycloheptane. The TB conformation of cylcoheptane has proven to be an extremely useful test for MINTA. In the test aimed at determining the integration volume (vide supra), several trial conformations in the $3\sigma$ hypercube were interconverted to the lower energy TC conformation. Senderowitz et al. also investigated cycloalkanes including cycloheptane to compare conformational free energy differences obtained by JBW and the harmonic approximation (rigid-rotor harmonic-oscillator (RRHO) model) (Senderowitz et al., 1995). It was concluded in their study that JBW could properly account for anharmonic effects, but generally the harmonic approximation was not so bad except for TB cylcoheptane. The free energy difference between TB and TC cycloheptane was found to be 1.66 kcal/mol (RRHO) and 2.8 kcal/mol (JBW), respectively (Senderowitz et al., 1995). Such a big difference between the JBW and the RRHO calculation is indicative of significant anharmonic effects. The following study was aimed at mapping the real shape of the TB cycloheptane PES to determine what is wrong with the harmonic approximation.

The adaptive implementation of importance sampling Monte Carlo integration provides a computational tool to trace the potential energy surface. The so-called VEGAS algorithm (Lepage et al., 1978; Press et al., 1992) operates by constructing, adaptively, a separable sampling function. The first iteration is simple Monte Carlo integration based on uniform sampling. However, the results of the function evaluations are saved and used to adjust the sampling function in subsequent iterations based on the fact that the optimal sampling function p |f| (vide supra). The sampling function is adjusted in subsequent iterations to preferentially sample regions where the magnitude of the integrand is large. The VEGAS algorithm has been implemented in the mode integration method with an important change. Instead of starting with uniform sampling, eq 4 is applied to initiate VEGAS. Unfortunately, VEGAS can only be used for up to ten dimensions (Press et al., 1992) and therefore cannot generally be used alone for the evaluation of molecular configuration integrals. However, it can be used to trace the potential energy surface in the directions of low-frequency modes. Since a converged VEGAS sampling function is proportional to the absolute value of the integrand, it is clear that a converged VEGAS iteration initiated from eq 4 affords a sampling function which is proportional to the exact partition function. In particular, the converged pieces of the separable sampling function (eq 4) trace the exact shape of one-dimensional slices of the partition function, aligned by the corresponding normal coordinate directions. For a quadratic potential, the exact shape is a Gaussian. Therefore, the deviation of the exact shape from the corresponding Gaussian reveals the nature of the anharmonic effect.

Figure 1:
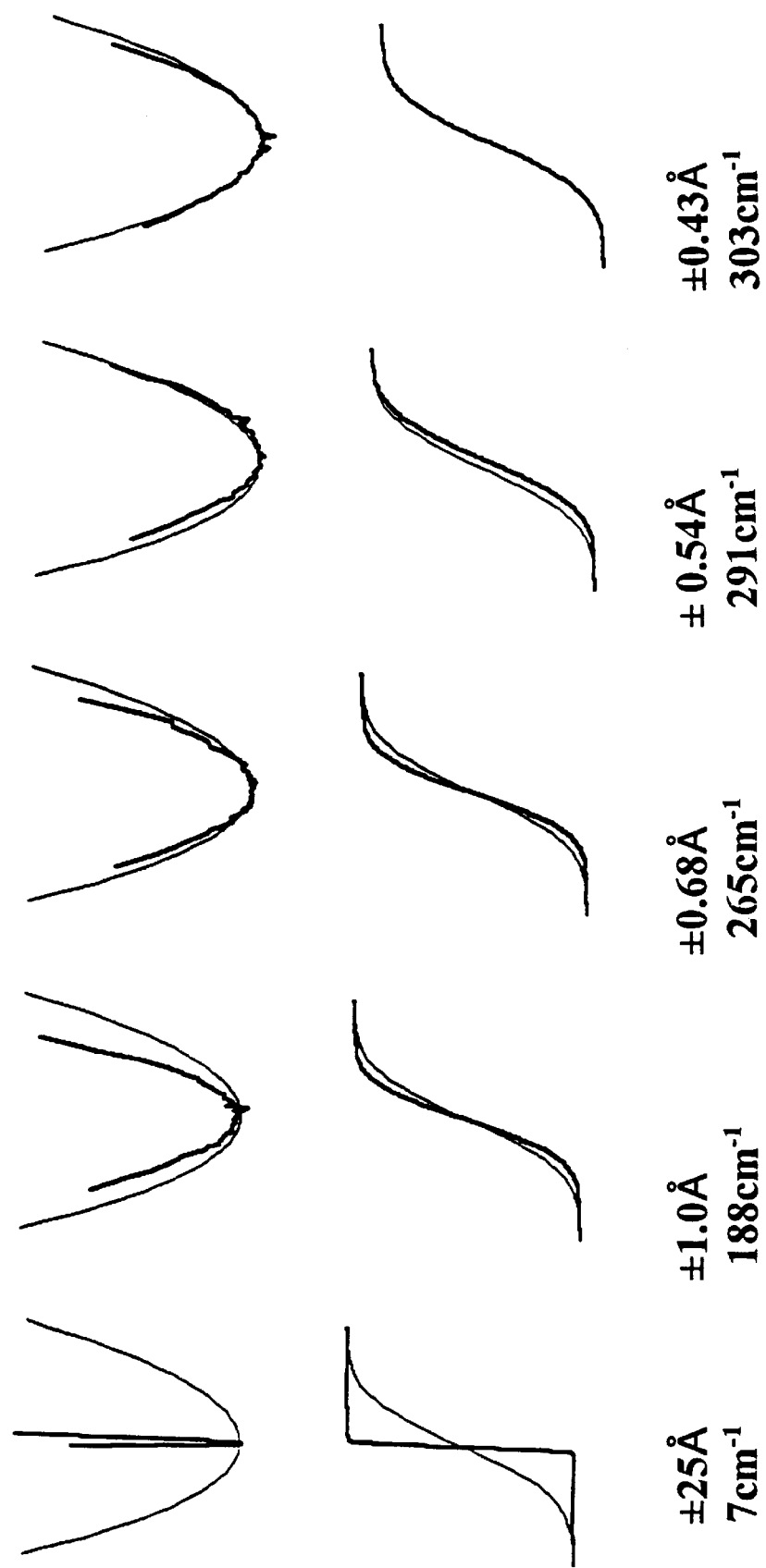
FIG. 1. Anharmonic effects in TB cycloheptane: true vs. harmonic one-dimensional PES slices. In the top row the thick lines delineate the exact shape of the potential surface along the first five low-frequency normal modes, and the thin lines show the corresponding harmonic potentials. In the bottom row the thick lines depict the true one-dimensional, cumulative partition functions and the thin lines show the corresponding cumulative Gaussians. The plots are autoscaled, the actual extent of the PES slices are given below the graphs along with the MM2 harmonic frequencies.

The results of a VEGAS calculation applied to the first ten low-frequency modes of TB cycloheptane are shown in FIG. 1. The first five modes are aligned from left to right. In the top row the thick lines delineate the exact shape of the potential surface derived from the VEGAS calculation along the corresponding normal modes, and the thin lines show the corresponding harmonic potentials. In the bottom row the thick lines depict the true one-dimensional partition functions and the thin lines show the corresponding Gaussians. Note that for better visualization the cumulative partition function is shown instead of the bell-shaped function defined in eq 4. Also note that the whole figure is autoscaled, the actual extent of the PES slices is given below the graphs. One glance at FIG. 1 immediately reveals what is wrong with the harmonic approximation. The very low MM2 (Allinger, 1977) frequency (7.0 cm$^{-1}$) is unrealistic. In fact, the corresponding 3σ hypercube extends to a spurious ±25 Å in the direction of this normal mode. Several other force fields and ab initio calculation also afforded similar, all too low frequencies: MM3 (Allinger et al., 1989) 21.9 cm$^{-1}$, AMBER (Weiner et al., 1984) 19.3 cm$^{-1}$, AMBER94 (Cornell et al., 1995) 29.4 cm$^{-1}$, OPLS (Jorgensen et al., 1988) 12.0 cm$^{-1}$, MMFF (Halgren, 1996) 25.1 cm$^{-1}$, and HF/6-31G* 22.3 cm$^{-1}$.

The real shape of the PES slice depicted by the thick line in FIG. 1 describes a much steeper PES. The real shape can be characterized by a fairly narrow, flat-bottom well. Note that it has been already known from free energy simulations that distorting a molecule along a single, extremely flat mode often results in "bumping" in a steep (potential) wall. However, until very recently, this phenomenon has been treated simply as "anharmonic effect" without further specification. Recent quantum mechanics calculations have shown that similar effects in a small protein (BPTI) can be attributed to anharmonicity of the low-frequency vibrational wave functions (Roitberg et al., 1995, 1997). In their work the authors presented a PES slice very similar to those shown in FIG. 1, by which they demonstrated that inclusion of the cubic and quartic diagonal terms of the Taylor expansion of the potential energy sufficed to trace the true PES along a low-frequency mode almost perfectly (Roitberg et al., 1997). They also stressed the experimental significance of the problem of "extreme flat modes" in a variety of vibrational spectroscopies.

In summary, the problem with the harmonic approximation in this case is that the very low frequency incorrectly suggests a shallow energy well based on the local curvature of the PES at the flat bottom. JBW gives the correct answer, because it samples the whole well, not only the flat bottom. For the same reason, mode integration should give the same correct answer with a suitable hypercube in eq 5. Therefore, a simple safeguard is used to prevent inadequate sampling due to flat-bottom wells. Generally, the 3σ rule is applied to the hypercube, but for extremely soft modes, the corresponding dimension of the hypercube is limited to ±3 Å. A MINTA calculation based on the 3σ/3 Å rule using 10,000 energy evaluations, sampling all degrees of freedom afforded 3.0 kcal/mol free energy difference between TB and TC cycloheptane, however, without the 3 Å limit the result was 3.2 kcal/mol.

The true shape of the PES slice associated with mode 4 (FIG. 1) exemplifies another anharmonic effect, namely, an asymmetrical energy well. However, it is clear that the higher modes are, in fact, vary close to be harmonic, the difference between the true PES slice and the corresponding harmonic potential completely vanishes from the fifth mode on. It has been shown recently that in a similar manner, the higher frequency modes of the protein BPTI are nearly harmonic (Roitberg et al., 1997; Go et al., 1983). This very fact suggests an astonishing simplification of MINTA: numerical integration of the soft modes and analytical integration of the hard modes based on the harmonic quantum oscillator model. Note that the "soft" modes are defined in a more general sense than just torsions (Head et al., 1997), representing low-mode conformational motions generally applicable to cyclic and cyclic molecules (Kolossváry et al., 1996; Kolossváry et al., 1993). The combined numerical/analytical MINTA algorithm involves the numerical integration of the soft modes via eqs 4, 5 (with or without VEGAS), and the analytical integration of the hard modes using the harmonic approximation. In all of the following calculations, however, MINTA was used to integrate all degrees of freedom numerically.

A value of methyl-, isopropyl- and methylphenylcyclohexane. The so-called A value of methylcyclohexane is the free energy difference between axial and equatorial methylcyclohexane. A values of numerous cyclohexane derivatives have been determined experimentally including isopropylcyclohexane and 1-methyl-1-phenylcyclohexane (Eliel et al., 1994). Recent JBW simulations afforded converged A values consistent with experiment (Senderowitz et al., 1995). Our MINTA calculations afforded virtually identical results summarized in Table 1.

Table 1. Calculated and Experimental A Values* of Methyl-, Isopropyl-, and 1-Methyl-1-phenylcyclohexane at 300 K

| | ΔG (kcal/mol)[2] MM2, in vacuo | | |
|---|---|---|---|
| | JBW (Senderowitz et al., 1995) | MINTA | Exp. (Senderowitz et al., 1995) |
| methyl | 1.9 | 1.9 | 1.6–1.8 |
| isopropyl | 2.6 | 2.4 | 2.0–2.4 |
| methyl-phenyl | −0.10 | 0.15 | ~0 |
| | 0.23[3] | 0.34[3] | 0.3[3] |

[1]A value = free energy differene between axial and equatorial substituted cyclohexane.
[2]Positive values favor the equatorial methyl, equatorial isopropyl and axial phenyl substituents, respectively.
[3]200K The MINTA calculations involved 10,000 function evaluations per conformation using the MM2 force field with infinite non-bonded cutoffs, in vacuo, and required only a few minutes of CPU time. It should be noted that FEP methods based on statistical mechanics generally perform well for similar systems in vacuum (Straatsma et al., 1992), however, MINTA is much faster. A recent, successful FEP simulation that involved the interconversion of chair conformers of methylcyclohexane by mutating an axial dummy atom and an equatorial united atom methyl into one another (using the AMBER force field) required 21 stages using stochastic dynamics and spanned a total of 4.2 ns to reach convergence (Senderowitz et al., 1995). The united atom (8 atoms) FEP simulation took 50 CPU minutes on a 250 Mhz R4400 processor, while the full atom (21 atoms) MINTA calculation described above took only a little over 1 CPU minute (a speed factor of ~43).

The MINTA integral estimates were calculated as block averages based on ten independent 1,000 point samples (Lepage, 1978). The resulting configuration integrals were all subject to less than 5% relative error (calculated as ±one standard deviation) (Lepage, 1978) which is equivalent to ±0.03 kcal/mol in free energy at room temperature. Note that the particularly good results in Table 1 are not only indicative of predictive power, but equally importantly, the remarkable agreement between JBW and MINTA results is the best cross-validation of these fundamentally different methods.

Anomeric free energy calculations. The successful test on A values prompted a series of significantly more difficult calculations of anomeric free energies. The modeling of carbohydrates has long been a particularly difficult problem, because conventional molecular mechanics force fields could not account for stereoelectronic effects resulting from the unique, condensed and highly polar structure of carbohydrates ((Melberg et al., 1979; Melberg et al., 1980; Rasmussen, 1982; Ha et al., 1988; Mardsen et al., 1988; Homans, 1990; Grootenhuis et al., 1993; Glennon et al., 1994; Woods et al., 1995; Asensio et al., 1995; Reiling et al., 1996; Csonka et al., 1997, Csonka et al., submitted for publication; Senderowitz et al., 1996). The anomeric free energy in particular, representing the free energy difference between the α and β stereoisomers of carbohydrates, can be measured experimentally, but has escaped calculations until very recently (Ha et al., 1991; Zheng et al., 1992; van Eijck et al., 1993; Schmidt et al., 1996; Senderowitz et al., 1996; Senderowitz et al., 1997). Especially, the introduction of carbohydrate parameters in the AMBER* (Mohamadi et al., 1990) force field based on ab initio calculations on pyranoses afforded a suitable force field for JBW calculations (Senderowitz et al., 1996). Therefore, a series of MINTA calculations have been carried out using the same AMBER* force field to calculate the anomeric free energy of tetrahydropyran derivatives, and pyranose monosaccharides glucose, methyl glucoside, mannose, methyl mannoside, galactose, 2-deoxyglucose, and N-acetylglucosamine. Once again, MINTA predictions were consistent with experiment and virtually identical to JBW predictions. The results are summarized on Table 2.

Table 2. Calculated and Experimental Anomeric Free energies of Tetrahydropyran Derivatives and Pyranose Monosaccharides at 300 K

| | ΔG (kcal/mol)[b] AMBER*, GB/SA water | | |
|---|---|---|---|
| | JBW (Senderowitz et al., 1996) | MINTA | Exp./ab initio (Senderowitz et al., 1996) |
| 2-hydroxy-tetrahyropyran | 0.28[c] | 0.40[c] | 0.69[c] |
| | −1.02 | −1.02 | −0.95 |
| 2-methoxy-tetrahydro-pyran | 0.65[c] | 0.68[c] | 0.94[c] |
| | 0.36[d] | 0.38[d] | 0.64 |
| | −0.41 | −0.35 | −0.7 to 0.1 |
| glucose | −0.22 | −0.11 | −0.34 |
| methyl glucoside | 0.53 | 0.59 | 0.42 |
| mannose | 0.21 | 0.21 | 0.34–0.45 |
| methyl mannoside | 1.34 | 1.35 | 1.70 |
| galactose | −0.03 | 0.10 | −0.37 |
| 2-deoxyglucose | −0.45 | −0.38 | −0.05 |
| N-acetylglucosamine | 0.50 | 0.52 | 0.51. |

[a]Anomeric free energy = free energy difference between α and β anomers.
[b]Positive values favor the α anomer.
[c]Invacuo.
[d]GB/SA chloroform.

The MINTA calculations were carried out with the united-atom AMBER* force field augmented with the new carbohydrate parameters (Senderowitz et al., 1996). Solvation treatment included the GB/SA (Still et al., 1990) continuum model with constant ($\in$=1) dielectric Coulomb equation and extended non-bonded cutoffs (20 Å for Coulomb and 8 Å for van der Waals interactions). The GB/SA model belongs to the family of continuum models (Eisenberg et al., 1986; Ooi et al., 1987; Kang et al., 1987; Warshel et al., 1984; Gilson et al., 1988; Still et al., 1990; Cramer et al., 1991) that have become popular alternatives to explicit (molecular) solvent models (Rossky et al., 1979; Jorgensen et al., 1983; Jorgensen et al., 1985) for the modeling of molecules in solution using molecular mechanics. Explicit solvent models, while exact in principle, are very expensive computationally, and are subject to random noise impeding convergence in FEP simulations. Furthermore, there is no compelling evidence that using contemporary force fields explicit solvent models are more accurate than continuum models (Marten et al., 1996). Therefore, the use of a continuum model for the calculation of anomeric free energies is justified. The GB/SA model in particular has been shown to afford comparable free energies of solventlike dielectric polarization for small organic molecules and peptides in water to those calculated by accurate but significantly slower Poisson-Boltzmann methods (Qiu et al., 1997; Edinger et ql., 1997).

The MINTA integrals were calculated as block averages based on 10×1,000 independent energy evaluations per conformation. The resulting anomeric free energies in Table 2 are subject to less than ±0.03 kcal/mol error. The MINTA calculations required 25–45 CPU seconds per conformation on a 75 Mhz R8000 processor.

Note that the pyranose monosaccharides have literally hundreds of conformations making it virtually impossible to claim a complete conformational search. Therefore, at first glance it seemed reasonable to use the exact same set of the one-hundred lowest-energy conformations for the MINTA calculation that were originally used for the JBW simulation (Senderowitz et al., 1996), to ensure unbiased comparison. However, the resulting MINTA anomeric free energies were off by up to 0.5 kcal/mol with respect to the JBW results. A more careful look at the JBW algorithm explains the discrepancy. The basic tenet of JBW is to interconvert conformations found in a preceding search, using an internal coordinate transformation matrix. However, JBW also involves small random variations of the internal coordinates and it is also coupled with stochastic dynamics (Senderowitz, 1995, 1996). This means that JBW, in fact, explores more of the conformational space than just the conformations used to seed the JBW simulation. Of course, this also means that MINTA which is restricted to the conformations at hand, should utilize all of the low-energy conformations found by the preceding search. Therefore, the MINTA calculations were repeated utilizing the full set of conformations found during the conformational search. Indeed, the results shown in Table 2 are in astonishing agreement with JBW! The largest difference is only ±0.13 kcal/mol (galactose) and for half of the molecules the differences is within the ±0.03 kcal/mol error bar. It should be noted, once again, that such remarkable agreement of two entirely different methods on a difficult problem cross-validates them by any standard.

Conclusions

The calculation of conformational free energies is one of the key issues in computational chemistry. In this paper, a novel theoretical approach is proposed for the direct calculation of conformational free energies without the need for expensive free energy simulations and the use of computational alchemy (Straatsma et al., 1992). The new MINTA algorithm is based on a particularly efficient implementation of importance sampling Monte Carlo integration, to solve the molecular configuration integral in all degrees of freedom. The MINTA method was applied here to study anharmonic effects in cycloheptane, and to predict the A value of cyclohexane derivatives and the anomeric free energy of carbohydrates (tetrahydropyran derivatives and pyranose monosaccharides). The MINTA calculation showed that the harmonic approximation was not applicable to TB cycloheptane, because the shape of the true potential energy surface along the lowest frequency normal mode can be characterized by a narrow, flat-bottom well. The MINTA predictions on the A values and the anomeric free energies were virtually identical with those obtained by converged JBW free energy simulations. For the calculation of the A value of methylcyclohexane, MINTA was at least 43 times faster than FEP. It should also be stressed that although inaccuracies in the computational methods and force fields have much room for improvement, and good agreement with experiment can always be attributed, at least to some extent, to cancellation of error, 0.5 kcal/mol or better accuracy is well within the range of serious interest for experimentalists. In recent studies MINTA has been shown to reproduce experimental binding free energies of enantioselective binding of small peptides to synthetic hosts to within the same <0.5 kcal/mol accuracy. In conclusion, MINTA should find wide utility for direct conformational free energy calculations.

EXAMPLE 2

(MINTA 2) Evaluation of the Molecular Configuration Integral in All Degrees of Freedom for the Direct Calculation of Binding Free Energies: Application to the Enantioselective Binding of Amino Acid Derivatives to Synthetic Host Molecules A novel theoretical approach is presented herein for the direct calculation of conformational free energies without the need for expensive free energy simulations. The new algorithm termed mode integration (MINTA) is based on a particularly efficient implementation of importance sampling Monte Carlo integration. MINTA allows, for the first time, to solve the molecular configuration integral of molecular complexes of real chemical interest, in all degrees of freedom utilizing a continuum salvation model. The MINTA method was applied here to predict the enantioselective binding of α-amino acid derivatives to podand ionophore hosts, and peptide ligands to $C_3$-symmetric synthetic receptors. In one particular case, the correct MINTA prediction of a significant, 1.5 kcal/mol entropic stabilization of the L-Ala peptide ligand with respect to its D-Ala enantiomer in binding to the receptor was elucidated by electronic structure calculations.

The statistical-thermodynamic foundation of the calculation of binding affinities of molecular complexes is quite complex (Gilson et al., 1997), but for most practical problems, the stability of host-guest complexes can be formulated in terms of binding free energy (BFE) differences (Gilson et al., 1997). For example, one wishes to calculate the BFE difference ($\Delta\Delta G_{L-D}=\Delta G_L-\Delta G_D$) between the L and D enantiomers of a ligand bound to an enantioselective host. The direct calculation of $\Delta\Delta G_{L-D}$, in the classical sense, involves the evaluation of the molecular configuration integral Q:

$$Q_L = \sum_{i=1}^{n_L} \int_{V_i^L} e^{-\frac{E(r)-E_0}{RT}} dr, \qquad \text{(Equation 6)}$$

$$Q_D = \sum_{i=1}^{n_D} \int_{V_i^D} e^{-\frac{E(r)-E_0}{RT}} dr$$

$$\Delta\Delta G_{L-D} = -RT \ln \frac{Q_L}{Q_D} \qquad \text{(Equation 7)}$$

It is assumed throughout that the dominant part of the configuration integral comes from contributions at or near to low-energy binding conformations (Kolossváry, submitted for publication; Gilson et al., 1997) (It is understood that the dominance of the low-energy conformations at room temperature is not generally true, especially for peptides. The conformational search results, however, suggest that this approximation is feasible for the binding calculations presented here.). Therefore, Q is summed over, respectively $n_L$ and $n_D$ conformations each encompassing different V volumes of the conformational space. E(r) is the molecular mechanics energy with respect to the nuclear coordinates r. E(r) includes the salvation energy as well, preferably in terms of a continuum model which does not introduce new degrees of freedom by explicit solvent molecules. $E_0$ is the global minimum energy, which is the common reference for both L and D binding conformations. R is the gas constant and T is the absolute temperature.

Figure 2:
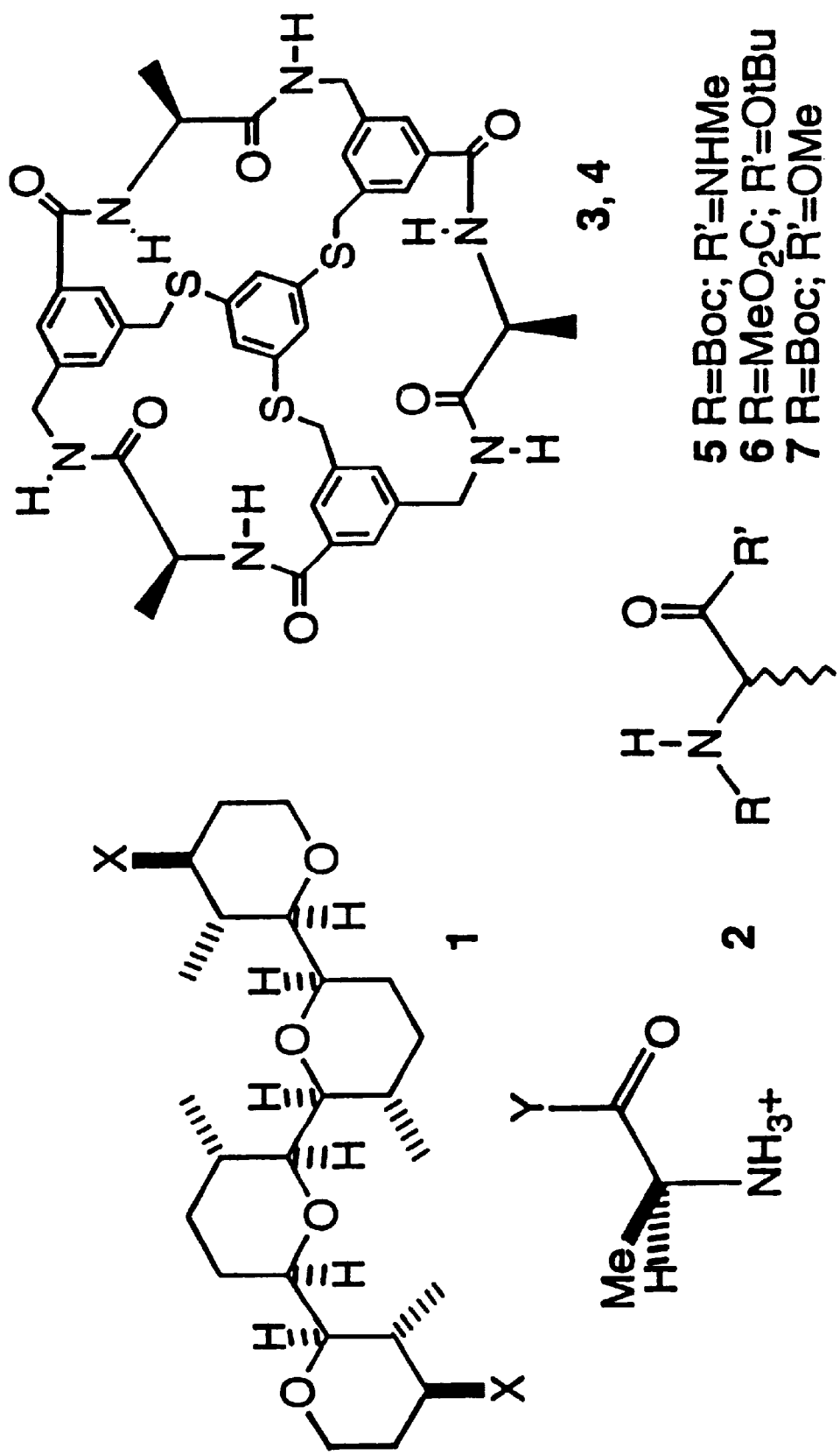
FIG. 2: Structural formual of compounds 1–7.

The first binding calculation reported here involves predicting the binding selectivity of podand ionophore 1 for enantiomeric α-amino acid derivatives 2 in chloroform (see FIG. 2). 1 is a good test case for BFE calculations, because earlier calculations based on simple energy minimization and evaluation of average energy at 300 K failed to reproduce experimental enantioselectivities (Lipkowitz et al., 1992). The MINTA results are given in Table 3 for four 1–2 systems for which experimental as well as computational (free energy perturbation) binding data have been previously reported (Burger, et al., 1994). The conformational search for locating the low-energy binding conformations was carried out by the particularly efficient conformational search procedure termed low-mode conformational search (LMOD) (Kolossváry et al., 1996). The LMOD conformations search included 5,000 Monte Carlo-energy minimization (MC/EM) steps utilizing the united atom AMBER* force field (Weiner et al., 1984; McDonald et al., 1992) and the GB/SA continuum solvation model (Still et al., 1990) for chloroform in BatchMin® V5.5 (Mohamadi et al., 1990), using a 50 kJ/mol energy window above the global minimum. The individual, conformational contributions to the molecular configuration integral in equation 6 were calculated by the combined numerical/analytical MINTA algorithm. The combined MINTA procedure involved the numerical integration of the fifty lowest-frequency (soft) vibrational modes and analytical integration if the remaining (hard) modes using the harmonic approximation. Note that the soft modes per se included contributions from the relative translation and rotation of 2 with respect to 1. It should also be stressed that the LMOD-MINTA procedure was applied to unconstrained host-guest systems to make sure that both the host and the ligand were fully sampled. Table 3: Calculated and Experimental Binding Free Energy Differences ($\Delta\Delta G_{L-D}$, kcal/mol) for Enantioselective Binding of 1 and 2 at 300 K.

| | | | $\Delta\Delta G_{L-D}$[1] AMBER*, GB/SA$_{CHCl_3}$ | | |
|---|---|---|---|---|---|
| X (1) | Y (2) | No. Of confs.[2] | FEP (Burger et al., 1994) | MINTA[3] | Exp. (Burger et al., 1994) |
| H | OMe | 292$_L$, 260$_D$ | −0.30 | −0.65 | −0.4 |
| NHAc | OMe | 358$_L$, 412$_D$ | −0.64 | −0.85 | −0.8 |
| NHAc | NHMe | 235$_L$, 270$_d$ | −0.96 | −1.31 | −1.1 |
| β-acetamido-butenolide | NHMe | 28$_L$, 33$_D$ | −1.90 | −1.95 | −1.7 |

[1]Negative values favor the L-2 enantiomer.
[2]The numbers include symmetric doublets (where found) reflecting the $C_2$ symmetry of 1.
[3]The MINTA integrals were calculated as block averages based on 10X1,000 independent energy evaluations per conformation. The resulting configuration integrals were all subject to less than 15% relative error which is equivalent to ±0.08 kcal/mol in free energy at room temperature.

The MINTA results gave the observed preference and affinity of 1 for binding L-amino acid derivatives, and are also in excellent agreement with converged free energy perturbation (FEP) simulations (Burger et al., 1994). It should be noted that even though the structure of 1 seems to be frozen by chiral centers and interlocking rings, in fact, the first three, moderately enantioselective 1–2 complexes afforded several hundred binding conformations within the lowest 50 kJ/mol. Timing data of the FEP simulation of the most strongly binding complex suggest that MINTA is at least four-times faster than FEP for this calculation.

The MINTA method was also applied to calculate the BFE differences of L- and D-alanine-derived peptides 5–7 binding to C3-symmetric synthetic receptors 3 and 4 (see FIG. 2) (hosts 3 and 4 are atropisomers) (McDonald et al., 1996). The LMOD-MINTA calculations were carried out with the same conditions used for the podand calculations above, but a smaller, 25 kJ/mol energy window was applied for the LMOD search to keep the number of conformations within reasonable limits.

The results are given in Table 4 for four systems.
Table 4: Calculated and Experimental Binding Free Energy Differences ($\Delta\Delta G_{L-D}$, kcal/mol) for Enantioselective Binding of 3 and 4 with Alanine-Derived peptides at 300 K

| | | | $\Delta\Delta G_{L-D}$[1] AMBER*, GB/SA$_{CHCl_3}$ | | |
|---|---|---|---|---|---|
| receptor | ligand | No. of confs.[2] | FEP (McDonald et al., 1996) | MINTA[3] | Exp. (McDonald et al., 1996) |
| 3 | Boc-Ala-NHMe (5) | 179$_L$, 226$_D$ | −2.4 | −2.3 | −2.2 |
| 3 | MeO$_2$C-Ala-OtBu (6) | 102$_L$, 53$_D$ | −2.6 | −2.0 | −2.5 |
| 3 | Boc-Ma-Ome (7) | 343$_L$, 265$_D$ | −1.1 | −0.30 | −0.3 |
| 4 | Boc-Ala-NMMe (5) | 146$_L$, 306$_D$ | −0.43 | −0.17 | 0.0 |

[1]Negative values favor the L-Ala enantiomer.
[2]The numbers include symmetric triplets (where found) reflecting the $C_3$ symmetry of hosts 3 and 4.
[3]The error of the MINTA calculations is ±0.08 kcal/mol (see Table 3, note 3).

Figure 3:
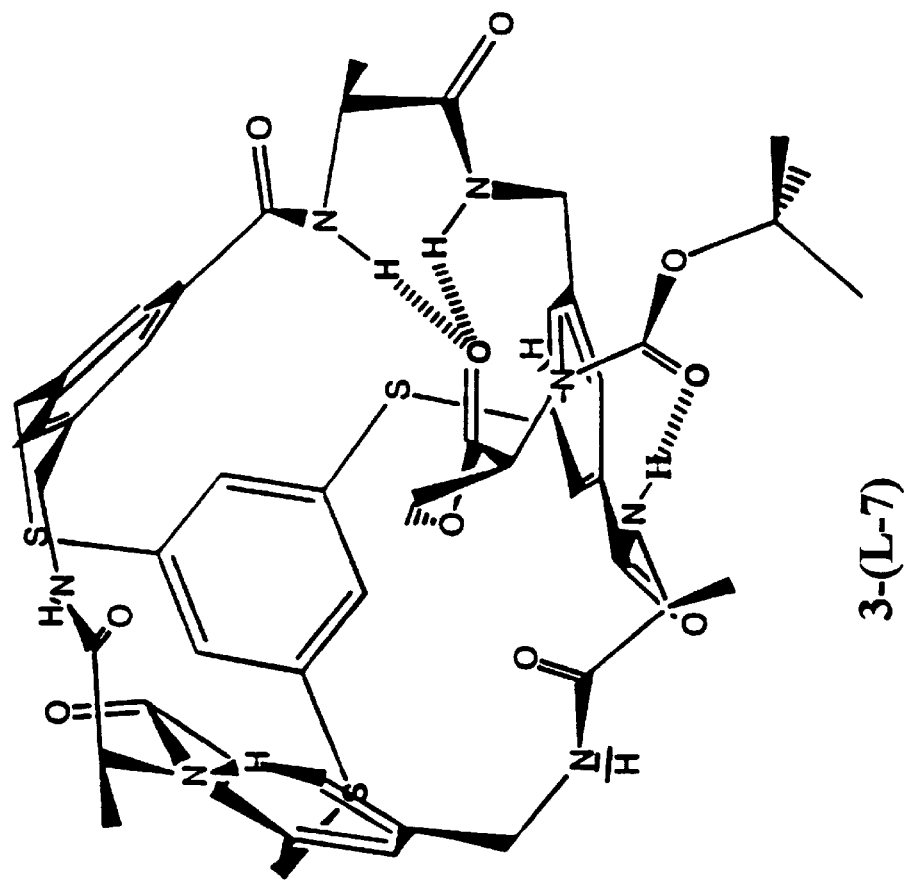
FIG. 3: Hydrogen bond tethers in number 3-(D-7) and 3-(L-7).
Figure 3:
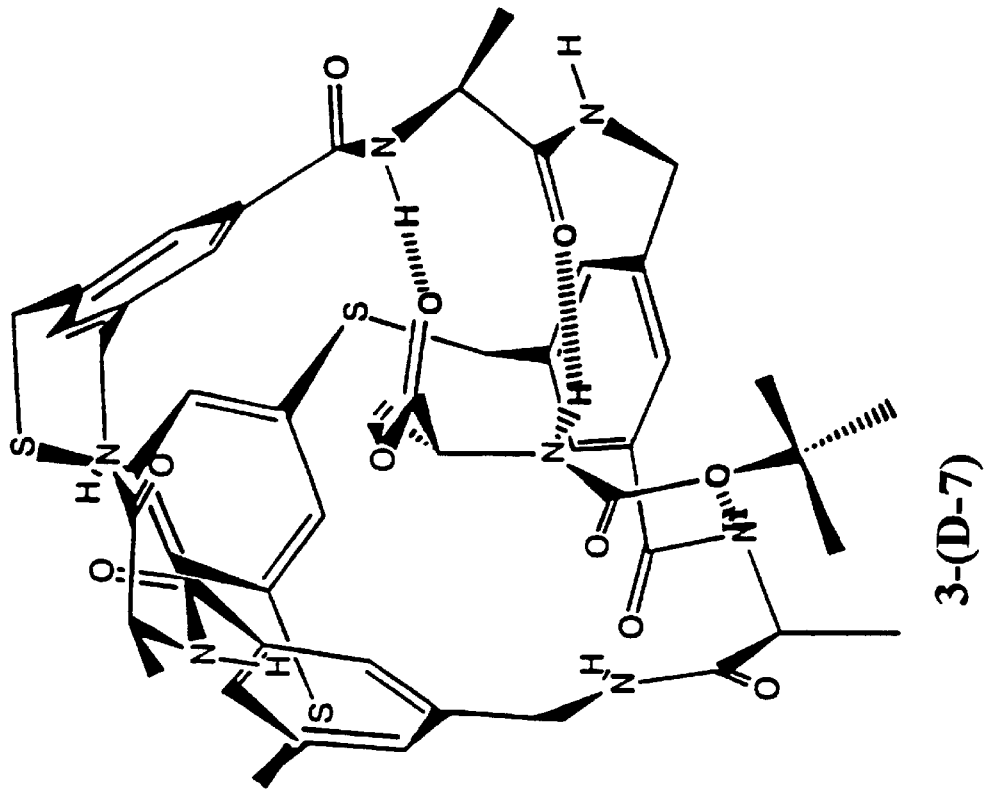

3 is strongly enantioselective with respect to 5, but its atropisomer 4 binds L-5 and D-5 with virtually the same affinity. MINTA reproduced the experimental enantioselectivity of both systems within 0.2 kcal/mol, but FEP was less successful with the weakly binding 4–5 complex despite the fact that the FEP simulation was running twice as long (1000 ps) for 4–5 than for 3–5 (McDonald et al., 1996). 3–6 is the most strongly binding complex, and FEP was slightly better than MINTA for this system. The most interesting system, however, is 3–7, because the moderate enantioselectivity of 3 favoring L-7 can be rationalized in terms of particularly strong entropic effects. The global minimum energy (enthalpy) binding conformation of 3–7 involves D-7 ligand, but the global minimum free energy binding conformation involves L-7 ligand. The enthalpy difference between them is $\Delta H=0.7$ kcal/mol favoring D-7, but the free energy difference is $\Delta G=0.8$ kcal/mol favoring L-7. The resulting 1.5 kcal/mol entropic stabilization of L-7 can be rationalized by the entirely different host-guest hydrogen bonding patterns shown in FIG. 3. D-7 ligand is locked into a rigid binding conformation by three H-bonds, while L-7 ligand is effectively tethered at only one point (Single point AM1 calculations were carried out using MOPAC® (Stewart, 1990), and the ENPART command was used to partition the energy into its integral subcomponents. The two-center integral contributions spanning between a particular H-bond acceptor and its hydrogen and donor atom, respectively, were summed to model the corresponding H-bond interaction, following a partitioning scheme recently introduced for analyzing hydrogen bonding networks. It has been found that one of the bonds of the bifurcating H-bond in the L-7 complex is 1.5–4 times weaker than the host-guest H-bonds in the D-7 complex and, in fact, the other bond is even repulsive, allowing almost free internal and external rotational variations for L-7. Experimental evidence for the enthalpy-entropy compensation for the complexation of the 3–7 system is achieved through measurements such as complementary binding enthalpy and entropy measurements. Hydrogen bonding patterns similar to those of 3–7 were found via $^1$H NMR for Boc, amino acid N-methylamides bound to 3 (Liu et al., 1993; Still et al., 1993), providing at least indirect experimental support for our H-bond analysis).

Similar entropic stabilization effects can play an important role in biological ligand-receptor interactions. It should also be noted that the experimental −0.3 kcal/mol enantioselectivity could only be reproduced by MINTA. FEP and the harmonic oscillator model significantly overestimated it (−1.1 and −0.78 kcal/mol, respectively), while a simple calculation that included only the minimized steric energy and GB/SA solvation free energy of the structures, incorrectly favored the enantioselective binding of D-7 by 0.28 kcal/mol.

The utility of the MINTA method has been demonstrated in binding free energy calculations for diverse molecular systems, for which MINTA has performed as well or better than free energy perturbation. In its current implementation, MINTA does not include solvation effects via explicit solvent models, and it is limited to approximately 250 freely moving atoms. However, utilizing continuum solvation models such as GB/SA (Still et al., 1990), and the application of grid based method (Hodge et al., 1995), can increase the effective number of atoms to several thousands including realistic solvation treatment. Therefore, MINTA should find wide utility for calculating relative binding affinities of drug molecules binding to a macromolecular host in biological systems.

EXAMPLE 3

MINTA: A Method for Calculating the Conformational Free Energy of Individual Molecules and Molecular Complexes to Predict the Relative Stability of Different Molecules and the Binding Affinity of Different Molecules for Another Molecule or Molecular Complexes A further explanation of MINTA follows. Mode Integration (MINTA) relies upon an exhaustive conformational search of the low-energy minima and the Monte Carlo integration of the molecular configuration integral over the individual conformational basins (eq 1) of the potential energy surface (PES). Simple Monte Carlo integration (see Press et al., 1992) utilizes the following theorem to estimate the integral of a function f over a multidimensional volume V:

$$\int_V f(r)\,dr \approx V\langle f\rangle \pm V\sqrt{\frac{\langle f^2\rangle - \langle f\rangle^2}{N}} \quad \text{(Equation 8)}$$

where < > refers to averages based on N function evaluations at randomly chosen points, uniformly distributed in volume V. The standard deviation (right hand side of eq 8) provides a rough estimate for the error of the integral. The problem with simple Monte Carlo integration is that for more than about half a dozen dimensions, a prohibitively large number of function evaluations is required to keep the error reasonably low. Advanced Monte Carlo integration methods based on stratified sampling and importance sampling, afford better integral estimates than simple Monte Carlo integration by reducing the standard deviation in eq 8 without the need for a prohibitive number of function evaluations.

The fundamental difference between importance sampling and simple Monte Carlo integration is that the random points used for function evaluations, are non-uniformly distributed. Importance sampling is based on a sampling function which, if chosen carefully, reduces the standard deviation of the Monte Carlo integral estimate significantly:

$$\int_V f(r)\,dr = \int_V \left(\frac{f(r)}{p(r)}\right) p(r)\,dr \quad \text{(Equation 9)}$$

$$\approx \left\langle \frac{f}{p}\right\rangle \pm \sqrt{\frac{\langle f^2/p^2\rangle - \langle f/p\rangle^2}{N}}$$

where the sampling function p is normalized. Note that eq 8 is a special case of eq 9, with p=1/V. It can be shown that the optimal choice for the sampling function is p |f,|, i.e., the more one knows about f the better one can estimate ∫f. The basic tenet of mode integration is to construct a sampling function which is very similar to the partition function (eq 1), in the vicinity of low-energy minima on the PES.

The obvious approach is to apply the harmonic approximation to each low-energy well on the PES by a local, second order Taylor expansion of the potential energy function (Karplus et al., 1981; Levy et al., 1984). The resulting sampling functions are normalized multivariate Gaussians:

$$P_i = \sqrt{\frac{\det H_i}{(2\pi RT)^n}} \exp\left(-\frac{1}{2RT}(r - r_i)H_i(r - r_i)\right) \quad \text{(Equation 3)}$$

where $r_i$ and $H_i$ denote, respectively, the bottom of a particular energy well and the associated local Hessian matrix. The Hessian is evaluated at the bottom of the well, The number of degrees of freedom n is equal to the number of unconstrained internal coordinates. Note that $p_i$ also depends on the temperature via RT.

Mode integration means, in essence, that eq 3 is utilized as a sampling function to integrate eq 1. However, for the reduction of the proposed theory in practice, one needs to consider two important issues: definition of the volume that is associated with a particular conformation in conformational space and to find an optimal coordinate system that guarantees the most accurate integral estimates. The optimal coordinate system can be derived by considering a simple fact about multivariate Gaussians. In real Gaussians, H is essentially the inverse of the covariance matrix which accounts for the correlation between the random variables of the multivariate Gaussian distribution. Unless the covariance matrix is diagonal, the off-diagonal elements give rise to mixed terms in the Gaussian exponential. However, by suitable coordinate transformation term principle component transformation, which is based on the diagonalization of the covariance matrix, the mixed terms can always be eliminated. The resulting Gaussian can be expressed as a product of n independent, univariate Gaussian functions. Analogously, a similar transformation can be applied to the Hessian matrix. The eigenvectors of the Hessian matrix $H_i$ span a local, orthogonal coordinate system centered at $r_i$, which is closely related to the normal modes of vibration. Utilizing the eigenvectors of the Hessian matrix in eq 3 results in a sampling function that can be expressed as a product of an independent, univariate Gaussian functions whose single variable represents the corresponding normal mode. Importance sampling based on the proposed, separable sampling function involves consecutively sampling n independent, one-dimensional Gaussian functions.

The normal mode coordinate system also provides a simple definition of the integration volume. The tail-off of one-dimensional Gaussians can be measured conveniently in units of standard deviation (σ). Approximately 68% of the underlying population is covered by ±σ, and 99.7% by ±3σ. In terms of a Gaussian partition function, this means that beyond three-four standard deviations the Boltzmann probability vanishes. Thus, the proposed multidimensional integration volume is a n-dimensional hypercube which is aligned along the normal modes, and whose dimensions depend on the harmonic vibrational frequencies as well as the temperature. Note that the integration volume is different for different conformations. MINTA therefore, utilizes the following separable sampling function for the Monte Carlo integration of the molecular configuration integral:

$$P_i = \prod_j^n \sqrt{\frac{\lambda_j}{2\pi RT}} \exp\left(-\frac{\lambda_j x_j^2}{2RT}\right) \quad \text{(Equation 4)}$$

where $j=1 \ldots n$ normal modes, $\lambda_1 \ldots \lambda_n$ are the eigenvalues of the non-mass-weighted Hessian matrix, and $x_1 \ldots x_n$ are the corresponding normal coordinates represented by the eigenvectors of the Hessian matrix. The center of the normal coordinate system is located at the bottom of the energy well where the gradient of the potential energy vanishes. $\sqrt{(RT/\lambda_j)}$ represents the quasi standard deviation of the Gaussian. Note that eq 4 refers to a single conformation i. Mode integration of the full molecular configuration integral involves integrating the individual, conformational partition functions via importance sampling using eq 4, and summing them up (eq 1):

$$Q = \sum_i^{n_{conf}} S_i \int_{\square_i} \left(\frac{e^{-\frac{E(x_i)-E_{0i}}{RT}}}{p_i}\right) p_i dx_i \quad \text{(Equation 5)}$$

$$\approx \sum_i^{n_{conf}} S_i \left\langle \frac{e^{-\frac{E(x_i)-E_{0i}}{RT}}}{p_i} \right\rangle_{\square_i}$$

where $p_i$ is the Gaussian sampling function (eq 4), $x_i$ is the vector of normal coordinates and $s_i$ is the symmetry number, of conformation i. The integration volume $\square_i$ is a n-dimensional hypercube with dimensions $d_j = 2$ const $\sqrt{(RT/\lambda_j)}$ measured in units of the quasi standard deviation (eq 4), $j=1 \ldots n$ and const is a multiplication factor. Note that in eq 5 $E_{0i}$, the reference for the energy difference in the Boltzmann exponential is the bottom of the individual energy wells, not the global minimum, $E_0$ (eq 1). Of course, this is only a matter of scaling. The right hand side of eq 5 is utilized to estimate the configuration integral by importance sampling inside the multidimensional hypercubes.

The essence of mode integration can be captured in a single sentence: The underlying idea that makes the method work is a novel use of the harmonic approximation for the particularly effective importance sampling of the true potential energy surface.

The following algorithmic description of the invention describes the calculation of the conformational or binding free energy of a single conformational family (defined hereinabove). In order to calculate the free energy difference between two conformational families, one has to apply the following algorithm to both families and then use equation 2 to get the free energy difference.

a. Do a conformational search to obtain the complete set of low-energy conformations of a single molecule of the low-energy binding conformations of a host-guest molecular complex, including all of the symmetry related copies as well as conformational enantiomers of a single conformation to account for the statistical correction for conformational symmetry. By "low-energy" it is meant that only the thermodynamically feasible conformations are included, i.e. conformation whose energy is within a specified energy window (typically 15–35 kJ/mol) above the global minimum energy found during the conformational search. For each and every conformation of the conformational family:

b. Determine the normal mode vectors (eigenvectors of the non-mass-weighted Hessian matrix, i.e., the matrix of the second derivatives of the energy with respect to the atomic coordinates).

c. Construct the sampling function using equation 4.

d. Evaluate the configuration integral using importance sampling Monte Carlo integration based on the sampling function. (C.) Over the multidimensional volume enclosing the current conformation in the conformational space.

NOTE that Monte Carlo integration can be applied to all of the degrees of freedom of the molecular system at hand, i.e. using all of the normal modes, or it can be applied to a subset of the normal modes. In the latter case, only a pre-defined number of the lowest frequency normal modes are included in the numerical Monte Carlo integration. The free energy contribution of the remaining, high frequency modes are calculated analytically, utilizing the well-known harmonic quantum oscillator model.

e. Apply equation 5 to evaluate the full configuration integral by summing up the individual, conformational contributions calculated in the loop (b–d).

NOTE that the individual, conformational free energy contributions are calculated with respect to the local minimum energy associated with the bottom of the energy well corresponding, respectively, to the different conformations on the potential energy surface (see text following equation 5).

Therefore:

f. Rescale each and every conformational contribution in the sum in equation 7 to reflect the free energy with respect to the global minimum energy.

G. Report the result as: the conformational (or binding) free energy of the conformational family at hand with respect to its global minimum by calculating $G=-RT\ln(Q)$ for the corrected Q (f).

H. In order to calculate the conformational, or binding free energy difference between two conformational families 1 and 2, carry out the MINTA algorithm (a.–g.) on both families and apply equation 2 to calculate the free energy difference.

NOTE that before applying equation 2, one of the Q's has to be corrected so that both Q1 and Q2 are expressed with respect to the single global minimum which can belong to either of the conformational families 1 or 2.

I. The previous algorithmic steps (a.–h.) assume that conformational families 1 and 2 belong to the same molecule or molecular complex (e.g.1=equatorial methyl-cyclohexane and 2=axial methyl-cyclohexane, or 1=alpha anomer and 2=beta anomer, or 1=L-ligand complexed with a host molecule and 2=D-ligand complexed with the same host molecule, etc.) However, the invention can be utilized for calculating the binding free energy difference between different molecular complexes as well. The most sought of problem for such a calculation is the estimation of the binding free energy difference $\Delta\Delta G$ of two different drug molecules with respect to the same protein host. In this case, the MINTA algorithm can be used in a straightforward manner following a thermodynamic cycle:

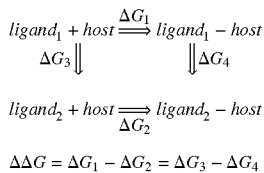

$$\Delta\Delta G = \Delta G_1 - \Delta G_2 = \Delta G_3 - \Delta G_4$$

Four independent conformational free energy calculations should be carried out using steps (a.-g.) on ligand$_1$, ligand$_2$, ligant$_1$-host and ligand$_2$-host, respectively, followed by the application of step (h.) to obtain $\Delta G_3$ and $\Delta G_4$. For $\Delta G_3$ 1 is ligand$_1$ and 2 is ligand$_2$. For $\Delta G_4$, 1 is ligand$_1$-host and 2 is ligand$_2$-host. The application of thermodynamic cycle is similar to free energy perturbation (FEP), but there is a fundamental difference. In FEP simulations, 1 is mutated into 2 in several steps requiring a fully converged simulation in each step, whereas the invention affords the $\Delta G$ between 1 and 2 in a single step.

Extensive calculations have been carried out to provide evidence for the usefulness of the invention. See for example Examples 1 and 2.

From the numerical results it is concluded that the invention is applicable to diverse molecular systems, and gives results that are virtually identical with those, or better than those obtained by existing free energy simulation techniques. Furthermore, the MINTA algorithm was more than ten times faster than FEP for the podand ionophore binding energy calculations, and two to three times faster than FEP in the synthetic peptide receptor calculations. Since MINTA afforded significantly better results than FEP in the latter case, for the weakly bound complexes, it can be concluded that a converged FEP simulation would have required a much longer simulation. Therefore, it can be concluded that the invention is likely more than ten times faster than free energy perturbation methods, especially, because MINTA was not optimized for speed in these test calculations.

The present invention is useful as a method for structure-based drug design. This is the first computational algorithm that affords a direct method for the calculation of conformational and binding free energies of molecular systems interesting for molecular engineering (particularly for rational drug design), without the need for expensive free energy simulations. The MINTA algorithm is devoid of convergence problems due to the sampling problem plaguing all of the simulation techniques simply, because MINTA treats the different conformations separately. Furthermore, the computational cost involved with the MINTA algorithm is significantly less than that of free energy simulations. The speed advantage of MINTA over simulation techniques is at least one order of magnitude that will potentially allow its use, for the first time, as a routine computational tool in the pharmaceutical industry.

An algorithm termed "mining minima" (Head et al.) has been described recently which is based on a similar concept. There are three fundamental differences between the invention and the "mining minima" method:
1. The "mining minima" method utilizes the traditional internal coordinates, i.e., bond lengths, bond angles and torsion angles, whereas the invention utilizes the so-call normal coordinates as described under THE INVENTION above.
2. The "mining minima" method ignores contributions to the conformational free energy from bond lengthening and bond angle bending, whereas the invention includes all of the conformational free energy contributions. This means that the "mining minima" method is inaccurate for ring systems where contributions to the free energy due to ring bond lengthening and angle bending is significant. The invention, however, can be used equally well for cyclic and acyclic systems. Furthermore, the "mining minima" method does not account for the free energy contribution die to the relative rotational and translational degrees of freedom of molecular complexes, and therefore, cannot calculate binding free energies. The invention, however, implicitly includes the free energy contribution due to the relative rotations and translations of two or more non-covalently bonded molecules and therefore, it can be used to calculate binding free energies which is, in fact, one of the most sought of kind of calculations in the pharmaceutical industry.
3. The "mining minima" method estimates the molecular configuration integral utilizing the simple Monte Carlo integration method, whereas the invention utilizes a novel, much more accurate importance sampling Monte Carlo integration method (See above). Because of the fast and accurate free energy calculation, the invention can potentially be applied to large molecular systems up to a few hundred freely moving atoms (a much larger number of atoms can be included in the calculation as "frozen" atoms representing the less mobile part of a large protein).

The present invention is embodied in software. It is coded in a computer program written in the C language which can be used as a plug-in module of the Batchmin® computational chemistry program package. The algorithm which is part of the subject matter of this invention is a novel combination of existing algorithms.

What is claimed is:
1. A method of using a computer processor to analyze electrical signals and data representative of a first molecule to determine conformational free energy of the first molecule so as to determine whether the first molecule is more stable than a second molecule, wherein both molecules have a predefined connectivity and exist in a predefined environment, comprising:
   (a) generating a set of data representative of low-energy minimum conformations of the first molecule derived from connectivity of the first molecule, a potential energy function, and a conformational search method;
   (b) determining conformational free energy of the first molecule by calculating a configuration integral in all degrees of freedom based upon a contribution of each conformation of the set of conformations of the first molecule, wherein the configuration integral is calculated by:
      (i) performing importance sampling multidimensional Monte Carlo integration over a multidimensional volume enclosing a current conformation of the first molecule in a conformational space,
      wherein the volume is dependent on harmonic vibrational frequencies of the current conformation and temperature,
      wherein the importance sampling comprises preferentially sampling regions of the volume in conformational space associated with the current conformation which regions have dominant contribution to the conformational free energy of the current conformation, and
      wherein the importance sampling utilizes a physical background consisting essentially of normal modes of vibration of the first molecule and the sampling is performed using an atomic coordinate transformation which is based on eigenvectors of a Hessian matrix associated with the current conformation;

(ii) repeating step (i) for each conformation in the set of data; and (iii) summing the conformational contributions determined in steps (i–ii) so as to determine a total configuration integral for the first molecule to determine the conformational free energy of the first molecule;

(c) repeating steps (a)–(b) for the second molecule; and (d) comparing the conformational free energy of the first molecule with the conformational free energy of the second molecule and determining which molecule has lower conformational free energy to determine which molecule is more stable.

2. The method of claim 1, wherein the low-energy minimum conformations are from about 15 kiloJoules per mole to about 35 kiloJoules per mole with respect to a lowest energy conformation.

3. The method of claim 1, wherein the potential energy function is based on molecular mechanics, semi-empirical quantum mechanics, ab initio quantum mechanics or density functional quantum mechanics.

4. The method of claim 1, wherein atomic coordinates comprise internal atomic coordinates or external atomic coordinates.

5. The method of claim 4, wherein the external atomic coordinates comprise Cartesian coordinates.

6. The method of claim 4, wherein the internal atomic coordinates comprise bond lengths, bond angles, or torsional angles.

7. The method of claim 1, wherein the Hessian matrix comprises an exact Hessian matrix or an approximation of an exact Hessian matrix.

8. The method of claim 1, wherein the first molecule comprises a molecular complex.

9. The method of claim 1, wherein the second molecule comprises a molecular complex.

10. The method of claim 1, wherein the environment comprises presence of solvent, a vacuum, or presence of a third molecule.

11. The method of claim 1, wherein either the first molecule or the second molecule or both molecules are subjected to extrinsic forces from the environment.

12. The method of claim 1, wherein the first molecule comprises a cyclic or an acyclic molecule.

13. The method of claim 1, wherein the second molecule comprises a cyclic or an acyclic molecule.

14. The method of claim 1, wherein the first molecule and the second molecule move with respect to one another.

15. The method of claim 1, wherein the first molecule comprises water, a biopolymer, a bio-oligomer, a protein, an enzyme, a peptide, a nucleic acid, a carbohydrate, a glycoprotein, a receptor, a lipid bilayer, a bio-compatible polymer, a metal, an organic compound, an inorganic compound, a natural product, a pharmaceutical compound, a drug or a drug candidate.

16. The method of claim 1, wherein the second molecule comprises water, a biopolymer, a bio-oligomer, a protein, an enzyme, a peptide, a nucleic acid, a carbohydrate, a glycoprotein, a receptor, a lipid bilayer, a bio-compatible polymer, a metal, an organic compound, an inorganic compound, a natural product, a pharmaceutical compound, a drug or a drug candidate.

17. The method of claim 1, wherein the method is used to select a drug candidate.

18. A method of using a computer processor to analyze electrical signals and data representative of conformations of molecular complexes to select either a first molecule or a second molecule as the molecule with stronger binding affinity to a host molecule, wherein the molecules have predefined connectivities and exist in a predefined environment, comprising:

(a) generating four sets of data representative of low-energy minimum conformations of:
(1) the first molecule,
(2) the first molecular complex comprising the first molecule bound to the host molecule,
(3) the second molecule, and
(4) the second molecular complex comprising the second molecule bound to the host molecule, wherein each set of data is derived from:
(i) connectivity of the corresponding molecule or molecular complex,
(ii) a potential energy function, and
(iii) a conformational search method;

(b) determining conformational free energy of each set by calculating a configuration integral in all degrees of freedom based upon a contribution of each conformation of the set of conformations, wherein the configuration integral is calculated by:

(i) performing importance sampling multidimensional Monte Carlo integration over a multidimensional volume enclosing a current conformation in a conformational space, wherein the volume is dependent on harmonic vibrational frequencies of the current conformation and temperature, wherein the importance sampling comprises preferentially sampling regions of the volume in conformational space associated with the current conformation which regions have dominant contribution to the conformational free energy of the current conformation, and wherein the importance sampling utilizes a physical background consisting essentially of normal modes of vibration and is performed using an atomic coordinate transformation which is based on eigenvectors of a Hessian matrix associated with the current conformation;

(ii) repeating step (b) (i) for each conformation in each set; and (iii) summing conformational contributions determined in steps (b) (i–ii) separately for each set so as to determine a total configuration integral to determine a value representative of conformation free energy of the first molecule, the first molecular complex, the second molecule and the second molecular complex;

(c) calculating the difference between the conformational free energy value for the second molecule and the value for the first molecule and the difference between the value for the second molecular complex and the value of the first molecular complex, and subtracting the difference between the molecules from the difference between the molecular complexes so as to determine a total difference;

(d) determining the sign of the total difference calculated in step (c) and selecting the first molecule if the difference is negative or selecting the second molecule if the difference is positive so as to select the molecule with stronger binding affinity to the host molecule.

19. The method of claim 18, wherein the method is repeated with a third molecule and a third molecular complex being substituted for the molecule and molecular complex not selected.

20. The method of claim 18, wherein the low-energy minimum conformations are from about 15 kiloJoules per mole to about 35 kiloJoules per mole with respect to a lowest energy conformation.

21. The method of claim 18, wherein the potential energy function is based on molecular mechanics, semi-empirical quantum mechanics, ab initio quantum mechanics or density functional quantum mechanics.

22. The method of claim 18, wherein atomic coordinates comprise internal atomic coordinates or external atomic coordinates.

23. The method of claim 22, wherein the external atomic coordinates comprise Cartesian coordinates.

24. The method of claim 22, wherein the internal atomic coordinates comprise bond lengths, bond angles, torsional angles or relative spatial position of members of each molecular complex defined by three translational and three rotational degrees of freedom.

25. The method of claim 18, wherein the Hessian matrix comprises an exact Hessian matrix or an approximation of an exact Hessian matrix.

26. The method of claim 18, wherein the environment comprises presence of solvent, a vacuum, or presence of a third molecule.

27. The method of claim 18, wherein the molecules or the molecular complexes are subjected to extrinsic forces from the environment.

28. The method of claim 18, wherein the first molecule comprises a cyclic or an acyclic molecule.

29. The method of claim 18, wherein the second molecule comprises a cyclic or an acyclic molecule.

30. The method of claim 18, wherein the host molecule comprises a cyclic or an acyclic molecule.

31. The method of claim 18, wherein the first molecule or the second molecule, and the host molecule move with respect to one another.

32. The method of claim 18, wherein the first molecule comprises water, a biopolymer, a bio-oligomer, a protein, an enzyme, a peptide, a nucleic acid, a carbohydrate, a glycoprotein, a receptor, a lipid bilayer, a bio-compatible polymer, a metal, an organic compound, an inorganic compound, a natural product, a pharmaceutical compound, a drug or a drug candidate.

33. The method of claim 18, wherein the second molecule comprises water, a biopolymer, a bio-oligomer, a protein, an enzyme, a peptide, a nucleic acid, a carbohydrate, a glycoprotein, a receptor, a lipid bilayer, a bio-compatible polymer, a metal, an organic compound, an inorganic compound, a natural product, a pharmaceutical compound, a drug or a drug candidate.

34. The method of claim 18, wherein the host molecule comprises water, a biopolymer, a bio-oligomer, a protein, an enzyme, a peptide, a nucleic acid, a carbohydrate, a glycoprotein, a receptor, a lipid bilayer, a bio-compatible polymer, a metal, an organic compound, an inorganic compound, a natural product, a pharmaceutical compound, a drug or a drug candidate.

35. The method of claim 18, wherein the method is used to select a molecule as a drug candidate.

36. A method of using a computer processor to analyze electrical signals and data representative of conformations of molecular complexes to select either a first molecule or a second molecule as the molecule with stronger binding affinity to a host molecule, wherein the first and second molecules are sterioisomers and exist in a predefined environment, comprising:

(a) generating two sets of data representative of low-energy minimum conformations of:
  (1) the first molecular complex comprising the first molecule bound to the host molecule, and
  (2) the second molecular complex comprising the second molecule bound to the host molecule,
  wherein each set of data is derived from:
  (i) connectivity of the corresponding molecular complex,
  (ii) a potential energy function, and
  (iii) a conformational search method;

(b) determining conformational free energy of each set by calculating a configuration integral in all degrees of freedom based upon a contribution of each conformation of the set of conformations, wherein the configuration integral is calculated by:
  (i) performing importance sampling multidimensional Monte Carlo integration over a multidimensional volume enclosing a current conformation in a conformational space,
  wherein the volume is dependent on harmonic vibrational frequencies of the current conformation and temperature,
  wherein the importance sampling comprises preferentially sampling regions of the volume in conformational space associated with the current conformation which regions have dominant contribution to the conformational free energy of the current conformation, and
  wherein the importance sampling utilizes a physical background consisting essentially of normal modes of vibration and the sampling is performed using an atomic coordinate transformation which is based on eigenvectors of a Hessian matrix associated with the current conformation;
  (ii) repeating step (b) (i) for each conformation in each set; and
  (iii) summing conformational contributions determined in steps (b) (i–ii) separately for each set so as to determine a total configuration integral to determine a value representative of conformation free energy of the first molecular complex, and the second molecular complex;

(c) calculating the difference between the value for the second molecular complex and the value of the first molecular complex so as to determine a total difference;

(d) determining the sign of the total difference calculated in step (c) and selecting the first molecule if the difference is negative or selecting the second molecule if the difference is positive so as to select the molecule with stronger binding affinity to the host molecule.

37. An apparatus capable of analyzing electrical signals and data representative of a first molecule to determine conformational free energy of the first molecule so as to determine whether a first molecule is more stable than a second molecule, wherein both molecules exist in a predefined environment, comprising:

(a) means for generating a set of data representative of low-energy minimum conformations of the first molecule derived from connectivity of the first molecule, a potential energy function, and a conformational search method;

(b) means for determining conformational free energy of the first molecule by calculating a configuration integral in all degrees of freedom based upon a contribution of each conformation of the set of conformations of the first molecule, wherein the configuration integral is calculated by:

(i) means for performing importance sampling multi-dimensional Monte Carlo integration over a multi-dimensional volume enclosing a current conformation of the first molecule in a conformational space, wherein the volume is dependent on harmonic vibrational frequencies of the current conformation and temperature, wherein the importance sampling comprises preferentially sampling regions of the volume in conformational space associated with the current conformation which regions have dominant contribution to the conformational free energy of the current conformation, and wherein the importance sampling utilizes a physical background consisting essentially of normal modes of vibration of the first molecule and the sampling is performed using an atomic coordinate transformation which is based on eigenvectors of a Hessian matrix associated with the current conformation;

(ii) means for repeating step (i) for each conformation in the set; and (iii) means for summing conformational contributions determined in steps (i–ii) so as to determine a total configuration integral for the first molecule to determine the conformational free energy of the first molecule;

(c) means for repeating steps (a)–(b) for the second molecule; and (d) means for comparing the conformational free energy of the first molecule with the conformational free energy of the second molecule and determining which molecule has lower conformational free energy to determine which molecule is more stable.

38. An apparatus capable of analyzing electrical signals and data representative of conformations of molecular complexes to select either a first molecule or a second molecule as the molecule with stronger binding affinity to a host molecule, wherein the molecules have predefined connectivities and exist in a predefined environment, comprising:

(a) means for generating four sets of data representative of low-energy minimum conformations of:
(1) the first molecule,
(2) the first molecular complex comprising the first molecule bound to the host molecule,
(3) the second molecule, and
(4) the second molecular complex comprising the second molecule bound to the host molecule, wherein each set of data is derived from:
(i) connectivity of the molecule or the molecular complex,
(ii) a potential energy function, and
(iii) a conformational search method;

(b) means for determining conformational free energy of each set by calculating a configuration integral in all degrees of freedom based upon a contribution of each conformation of the set of conformations, wherein the configuration integral is calculated by:

(i) means for performing importance sampling multi-dimensional Monte Carlo integration over a multi-dimensional volume enclosing a current conformation in a conformational space, wherein the volume is dependent on harmonic vibrational frequencies of the current conformation and temperature, wherein the importance sampling comprises preferentially sampling regions of the volume in conformational space associated with the current conformation which regions have dominant contribution to the conformational free energy of the current conformation, and wherein the importance sampling utilizes a physical background consisting essentially of normal modes of vibration and is performed using an atomic coordinate transformation which is based on eigenvectors of a Hessian matrix associated with the current conformation;

(ii) means for repeating step (b) (i) for each conformation in each set; and (iii) means for summing conformational contributions determined in steps (b) (i–ii) separately for each set so as to determine a total configuration integral to determine a value representative of conformation free energy of the first molecule, the first molecular complex, the second molecule and the second molecular complex;

(c) means for calculating the difference between the conformational free energy value for the second molecule and the value for the first molecule and the difference between the value for the second molecular complex and the value of the first molecular complex, and subtracting the difference between the molecules from the difference between the molecular complexes so as to determine a total difference;

(d) means for determining the sign of the total difference calculated in step (c) and selecting the first molecule if the difference is negative or selecting the second molecule if the difference is positive so as to select the molecule with stronger binding affinity to the host molecule.

* * * * *